United States Patent
Ausiello et al.

(10) Patent No.: US 9,891,233 B2
(45) Date of Patent: Feb. 13, 2018

(54) METHODS FOR PREDICTING TIME-TO-DELIVERY IN PREGNANT WOMEN

(71) Applicant: N-Dia, Inc., Boston, MA (US)

(72) Inventors: Anthony Ausiello, Peabody, MA (US); Ruben Salinas, Andover, MA (US); Michael Thompson, Boston, MA (US); Daniel J. Mackey, Newton, MA (US); Kaitlyn Nardozzi, Brighton, MA (US); Michael Friedman, Tzphon Yehudah (IL)

(73) Assignee: N-Dia, Inc., Boston, MA (US)

( * ) Notice: Subject to any disclaimer, the term of this patent is extended or adjusted under 35 U.S.C. 154(b) by 0 days.

(21) Appl. No.: 15/186,140

(22) Filed: Jun. 17, 2016

(65) Prior Publication Data

US 2016/0291031 A1 Oct. 6, 2016

Related U.S. Application Data

(62) Division of application No. 14/138,753, filed on Dec. 23, 2013.

(Continued)

(51) Int. Cl.
*G01N 33/558* (2006.01)
*G01N 33/68* (2006.01)
(Continued)

(52) U.S. Cl.
CPC .......... *G01N 33/689* (2013.01); *C07K 16/18* (2013.01); *A61B 2010/0074* (2013.01);
(Continued)

(58) Field of Classification Search
None
See application file for complete search history.

(56) References Cited

U.S. PATENT DOCUMENTS

| 3,817,837 A | 6/1974 | Rubenstein et al. |
| 4,313,734 A | 2/1982 | Leuvering |

(Continued)

FOREIGN PATENT DOCUMENTS

| CN | 1697972 A | 11/2005 |
| EP | 0143574 A1 | 6/1985 |

(Continued)

OTHER PUBLICATIONS

International Search Report and Written Opinion in International Application No. PCT/US2013/77541, dated Mar. 21, 2014, (11 pages).

(Continued)

*Primary Examiner* — Chris L Chin
(74) *Attorney, Agent, or Firm* — Fish & Richardson P.C.

(57) ABSTRACT

The present disclosure relates to methods for predicting time-to-delivery in pregnant women. The methods include predicting that a pregnant woman will deliver within a predetermined time frame if PAMG-1 is determined to be present at a level above a predetermined detection threshold in a vaginal fluid sample obtained from the pregnant woman. Also provided are methods for determining a patient's risk of preterm labor and/or spontaneous rupture of the chorio-amniotic membrane.

12 Claims, 2 Drawing Sheets

Related U.S. Application Data

(60) Provisional application No. 61/748,310, filed on Jan. 2, 2013, provisional application No. 61/909,238, filed on Nov. 26, 2013.

(51) Int. Cl.
  *C07K 16/18* (2006.01)
  *A61B 10/00* (2006.01)

(52) U.S. Cl.
  CPC . *G01N 2333/471* (2013.01); *G01N 2800/368* (2013.01); *G01N 2800/50* (2013.01)

(56) References Cited

U.S. PATENT DOCUMENTS

| | | | |
|---|---|---|---|
| 4,366,241 A | 12/1982 | Tom et al. | |
| 4,373,932 A | 2/1983 | Gribnau et al. | |
| 4,376,110 A * | 3/1983 | David | G01N 33/576 435/5 |
| 4,632,901 A | 12/1986 | Valkirs et al. | |
| 4,703,017 A | 10/1987 | Campbell et al. | |
| 4,770,853 A | 9/1988 | Bernstein | |
| 4,806,312 A | 2/1989 | Greenquist | |
| 4,810,658 A | 3/1989 | Shanks et al. | |
| 4,857,453 A | 8/1989 | Ullman et al. | |
| 4,906,439 A | 3/1990 | Grenner | |
| 4,918,025 A | 4/1990 | Grenner | |
| 4,943,522 A | 7/1990 | Eisinger et al. | 435/7.25 |
| 4,946,778 A | 8/1990 | Ladner et al. | |
| 4,952,517 A | 8/1990 | Bahar | |
| 4,959,305 A | 9/1990 | Woodrum | 435/7.7 |
| 4,978,503 A | 12/1990 | Shanks et al. | |
| 4,981,768 A | 1/1991 | Monbaliu et al. | |
| 5,030,558 A | 7/1991 | Litman et al. | |
| 5,037,735 A | 8/1991 | Khanna et al. | |
| 5,051,237 A | 9/1991 | Grenner et al. | |
| 5,073,484 A | 12/1991 | Swanson et al. | |
| 5,114,673 A | 5/1992 | Berger et al. | |
| 5,132,405 A | 7/1992 | Huston et al. | |
| 5,137,808 A | 8/1992 | Ullman et al. | |
| 5,138,868 A | 8/1992 | Long | |
| 5,141,871 A | 8/1992 | Kureshy et al. | |
| 5,147,609 A | 9/1992 | Grenner | |
| 5,156,952 A | 10/1992 | Litman et al. | |
| 5,186,897 A | 2/1993 | Eason et al. | |
| 5,252,459 A | 10/1993 | Tarcha et al. | |
| 5,284,749 A | 2/1994 | Cowley et al. | |
| 5,308,775 A | 5/1994 | Donovan et al. | |
| 5,352,582 A | 10/1994 | Lichtenwalter et al. | |
| 5,354,692 A | 10/1994 | Yang et al. | 436/514 |
| 5,476,786 A | 12/1995 | Huston | |
| 5,554,504 A | 9/1996 | Rutanen | |
| 5,559,041 A | 9/1996 | Kang et al. | 436/518 |
| 5,597,700 A | 1/1997 | Konstantinov et al. | |
| 5,602,040 A * | 2/1997 | May | G01N 33/54386 422/401 |
| 5,622,871 A | 4/1997 | May et al. | 436/514 |
| 5,654,162 A | 8/1997 | Guire et al. | |
| 5,712,172 A | 1/1998 | Huang et al. | |
| 5,714,389 A | 2/1998 | Charlton et al. | |
| 5,728,587 A | 3/1998 | Kang et al. | |
| 5,747,273 A | 5/1998 | Khosravi et al. | |
| 5,807,690 A | 9/1998 | Sanders et al. | |
| 5,877,029 A | 3/1999 | Fuks et al. | |
| 5,891,722 A | 4/1999 | Fuks et al. | |
| 5,968,758 A | 10/1999 | Fuks et al. | |
| 5,989,921 A | 11/1999 | Charlton et al. | |
| 6,020,147 A | 2/2000 | Guire et al. | |
| 6,348,323 B1 | 2/2002 | Khosravi et al. | |
| 6,485,982 B1 | 11/2002 | Charlton | |
| 7,709,272 B2 | 5/2010 | Fuks et al. | |
| 8,114,027 B2 * | 2/2012 | Triva | A61B 10/0045 435/283.1 |
| 8,114,610 B2 | 2/2012 | Fuks et al. | |
| 2005/0136490 A1 | 6/2005 | Rutanen | |
| 2012/0009609 A1 | 1/2012 | Fuks et al. | |
| 2012/0135432 A1 | 5/2012 | Rutanen | |
| 2013/0071865 A1 * | 3/2013 | Fuks | G01N 33/558 435/7.94 |
| 2014/0011220 A1 | 1/2014 | Fuks et al. | |
| 2016/0327565 A1 * | 11/2016 | Fuks | G01N 33/558 |
| 2017/0023582 A1 | 1/2017 | Fuks et al. | |

FOREIGN PATENT DOCUMENTS

| | | |
|---|---|---|
| EP | 0229359 A1 | 7/1987 |
| EP | 0316919 A2 | 5/1989 |
| EP | 0281327 B1 | 6/1993 |
| EP | 0280559 B1 | 10/1993 |
| EP | 0362809 B1 | 1/1994 |
| EP | 0299428 B1 | 1/1996 |
| EP | 0565541 B1 | 12/1997 |
| EP | 0560411 B1 | 7/2000 |
| JP | 2004528036 | 9/2004 |
| JP | A-2005-535887 | 11/2005 |
| JP | A-2010-518058 | 5/2010 |
| RU | 1614194 | 5/1998 |
| RU | 2110800 | 5/1998 |
| WO | WO 88/08534 | 11/1988 |
| WO | WO 89/12690 | 12/1989 |
| WO | WO 92/12426 | 7/1992 |
| WO | WO 99/46597 | 9/1999 |
| WO | WO 2004/014220 | 2/2004 |
| WO | WO2004014220 A2 | 2/2004 |
| WO | WO 2008/096122 | 8/2008 |
| WO | WO2009018607 A1 | 2/2009 |
| WO | WO 2010/020043 | 2/2010 |

OTHER PUBLICATIONS

Japanese Examination Report dated Feb. 2, 2010 for Japanese counterpart Application Serial No. 2004-528036 filed Aug. 12, 2003, (6 pages).

Canadian IPO Search Report dated Apr. 14, 2010 for Canadian counterpart Application Serial No. 2,533,915 filed Aug. 12, 2003, (5 pages).

Indian Examination Report dated Jul. 27, 2010 for Indian counterpart Application Serial No. 5175/DELNP/2007 filed Jul. 4, 2007, (3 pages).

Notice of Opposition dated Sep. 18, 2013 for Application No. 10160487.4-1408 / 2204654, (31 pages).

DiRenzo, et al., *Guidelines for the management of spontaneous preterm labor: identification of spontaneous preterm labor, diagnosis of preterm premature rupture of membranes, and preventive tools for preterm birth*, The Journal of Maternal-Fetal and Neonatal Medicine, Early Online, 1-9 (2011).

Actim™ Prom, Qualitative Test for Detection of Amniotic Fluid in the Vagina, Instructions for Use, Medix Biochemica pamphlet, 1 page (2004).

Alexander and Cox, *Clinical Course of Premature Rupture of the Membranes*, Seminars in Perinatology, 20(5):369-374 (1996).

Allander, et al. The Proceedings of the $2^{nd}$ International Workshop of IGF Binding Proteins, Aug. 27-30, 1992, Opio, Cote d'Azur, France, Growth Regulation: *Gene Structures and Expressions, Structure and Chromosomal Localization of Human Insulin-like Growth Factor-Binding Protein Genes*, pp. 3-5 (1993).

AmniSure® ROM (Rupture of [fetal] Membranes) Test, Directions for In Vitro Diagnostic Use, 2 pages, (2010).

Ballard, et al., *Report on the Nomenclature of the IGF Binding Proteins*, Journal of Clinical Endocrinology and Metabolism, 70(3):817-818 (1990).

Bell, Stephen C., *Secretory endometrial and decidual proteins: studies and clinical significance of a maternally derived group of pregnancy-associated serum proteins*, Human Reproduction, 1(3):129-143 (1986).

Bell, and Keyte, *N-Terminal Amino Acid Sequence of Human Pregnancy-Associated Endometrial $a_1$-Globulin, an Endometrial Insulin-like Growth Factor (IGF) Binding Protein—Evidence for Two Small Molecular Weight IGF Binding Proteins*, Endocrinology, 123(2):1202-1204 (1988).

(56) References Cited

OTHER PUBLICATIONS

Bell, et al., *Regulation of Insulin-Like Growth Factor-Binding Protein-1 Synthesis and Secretion by Progestin and Relaxin in Long Term Cultures of Human Endometrial Stromal Cells*, Journal of Clinical Endocrinology and Metabolism, 72(5):1014-1024 (1991).
Bell, et at, *Monclonal Antibodies to Human Secretory "Pregnancy Associated Endometrial $\alpha_1$-Globulin," an Insulin-Like Growth Factor Binding Protein: Characterization and Use in Radioimmunoassay, Western Blots, and Immunohistochemistry*, American Journal of Reproductive Immunology, 20:87-96 (1989).
Berggard et al., *Histologic Distribution and Biochemical Properties of $\alpha_1$-Microglobulin in Human Placenta*, American Journal of Reproductive Immunology, 41:52-60 (1999).
Berggard, Tord, *Structure and distribution of alpha-l-microglobulin proteins*, Lund University Department of Cellular and Molecular Biology Section for Molecular Signalling, Doctoral Dissertation (abstract) (1998) (4 pages).
Bischof, Paul, *The Pregnancy Proteins (PP12, PP14, and PAPP-A): Their Biological and Clinical Relevance*, American Journal of Perinatology 6(2):110-116 (Apr. 1989).
Bohn, H., *Protein Antigens of the Human Placenta*, Proceedings of the Serno Symposia 35:23-34, (1980).
Bohn, and Kraus. *Isolation and Characterization of a New Placenta Specific Protein ($PP_{12}$)*, Arch. Gynecol. 229:279-291 (1980).
Bohn, et al., *New Soluble Placental Tissue Proteins: Their Isolation, Characterization, Localization and Quantification*, Immunology of Human Placental Proteins [Supplement 4], pp. 67-81, (1982).
Boltovskaya et al., *Histochemical and Clinical-Diagnostic Study of Placental $\alpha_1$-Microglobulin Using Monoclonal Antibodies*, Laboratory of Cellular Immunopathology and Biotechnology, Institute of Human Morphology, Academy of Medical Sciences of the USSR. Laboratory of Immunology, Moscow [Translated from Byulleten' Eksperimental'noi Biologii i Meditsiny] vol. 112, No. 10, pp. 397-400, Oct. 1991. Original article submitted Mar. 29, 1991.
Briese et al., *Circulating Levels of Placental Protein 12 (PP 12) in Diabetic Pregnancy Complicated by Retinopathy*, Exp. Clin. Endocrinol. 95(1):105-109 (1990).
Burdett et al., Proteins of human amniotic fluid. II. Mapping by two-dimensional electrophoresis, Clinical Chem., 28(4):935-940 (abstract) (Apr. 1982).
Busby, W.H. Jr. et al., *Purification of a 31,000-dalton insulin-like growth factor binding protein from human amniotic fluid. Isolation of two forms with different biologic actions*, J. Biol. Chem. 263(28):14203-14210 (1988).
Chen, et al., *Comparison of two rapid strip tests based on IGFBP-1 and PAMG-1 for the detection of amniotic fluid*, Amer. J. Perinatology, 25(4):243-246 (2008).
Cote et al., *Generation of human monoclonal antibodies reactive with cellular antigens*, Proc. Natl. Acad. Sci. USA, 80:2026-2030 (1983).
Cousins et al., *AmniSure Placental Alpha Microglobulin-1 Rapid Immunoassay versus Standard Diagnostic Methods for Detection of Rupture of Membranes*, American J Perinatology, 22:1-5 (2005).
Cubbage, et al., *Structure of the Human Chromosomal Gene for the 25 Kilodalton Insulin-Like Growth Factor Binding Protein*, Molecular Endocrinology 3:35:846-851 (1989).
Darj and Lyrenas, *Insulin-like growth factor binding protein-1, a quick way to detect amniotic fluid*, Acta. Obstet. Gynecol. Scand., 77:295-297 (1998).
Database search for PAMG-1, Database accessed Aug. 12, 2013, 1 page.
de Haan, et al., *Value of the fern test to confirm or reject the diagnosis of ruptured membranes in modest in nonlaboring women presenting with nonspecific vaginal fluid loss*, American J Perinatology, 11:46-50 (Jan. 1994).
Declaration under 37 C.F.R. 1.132 by Dr. Boris Fuks, dated Apr. 23, 2012 (36 pages).
Declaration under 37 C.F.R. 1.132 by Michael Friedman, dated Jun. 21, 2011 (9 pages).

Diamandi, et al., *Immunoassay of Insulin-Like Growth Factor-Binding Protein-3 (IGFBP-3): New Means to Quantifying IGFBP-3 Proteolysis*, Journal of Clinical Endocrinology and Metabolism, 85(6):2327-2333 (2000).
Ehrenborg, et al., *Contiguous Localization of the Genes Encoding Human Insulin-like Growth Factor Binding Proteins 1 (IGBP 1) and 3 (IGBP3) on Chromosome 7*, Genomics 12(3):497-502 (1992).
Eriksen et al., *Fetal fibronectin: a method for detecting the presence of amniotic fluid*, Obstetrics and Gynecology, 80(3)(Pt 1):451-454 (Sep. 1992).
Expert Opinion in the lawsuit 41 O 331/03, May 20, 2005; (12 pages) [English translation from German].
Gaucherand P, et al., *Comparative study of three vaginal markers of the premature rupture of membranes. Insulin like growth factor binding protein 1 Diamine-oxidase pH*, Acta Obstet Gynecol Scand., 76(6):536-540, (1997) PubMed PMID:9246958.
Giudice L., *Multifaceted roles for IGFBP-1 in human endometrium during implantation and pregnancy*, Annals of NY Acad Sci. 828:146-56, (1997) PubMed PMID: 9329833.
Guibourdenche J, et al., *Rapid detection of insulin-like growth factor binding protein-1 and fetal fibronectin in cervico-vaginal secretions to diagnose premature membrane rupture*, Ann Clin Biochem. 36(3):388-390 (1999) PubMed PMID: 10376083.
Hellemans, P. et al., *Preliminary results with the use of the ROM-check immunoassay in the early detection of rupture of the amniotic membranes*, European Journal of Obstetrics & Gynecology and Reproductive Biology, 43:173-179 (1992).
Jain and Morris, *A clinical study to evaluate the usefulness of the MAST test in diagnosing pre labour rupture of membranes* J Obstetrics and Gynaecology, 8(1):33-36 (1998) PubMed PMID: 15511998.
Jeurgens-Borst et al., *Use of insulin like growth factor binding protein-1 in the diagnosis of ruptured fetal membranes*, European Journal of Obstetrics & Gynecology and Reproductive Biology 102:11-14 (2002).
Kim, He-Seong et al., *Identification of a family of low-affinity insulin-like growth factor binding proteins (IGFBPs): Characterization of connective tissue growth factor as a member of the IGFBP superfamily*. Proc. Natl. Acad. Sci. USA 94(24):12981-12986 (1997).
Kishida, Tatsuro et al., *Diagnosis of premature rupture of the membranes in preterm patients, using an improved AFP kit: comparison with ROM-check and/or nitrazine test*, European Journal of Obstetrics & Gynecology and Reproductive Biology 69:77-82 (1996).
Koistinen, et al., *Placental Protein 12 is a Decidual Protein that Binds Somatomedin and Has an Identical NK-Terminal Amino Acid Sequence with Somatomedin-Binding Protein from Human Amniotic Fluid*, Endocrinology 118(4):1375-1378 (1986).
Koninckx, P.R. et al., *Prolactin Concentration in Vaginal Fluid: A New Method for Diagnosing Ruptured Membranes*, British Journal of Obstetrics and Gynecology 88:607-610 (1981).
Kubota, and Takeuchi, *Evaluation of Insulin-Like Growth Factor Binding Protein-1 as a Diagnostic Tool for Rupture of the Membranes*, J. Obstet. Gynaecol. Res. 24(6):411-417 (1998).
Ladfors L, *Is the use of IGFB-1 for diagnosing ROM of any clinical value*, Acta Obstet Gynecol Scand. 78(6):557-558 (1999) PubMed PMID: 10376870.
Lee and Yoon, *Comment and reply on: the clinical significance of a positive Amnisure test in women with term labor with intact membranes*, Letters to the editor, The Journal of Maternal-Fetal and Neonatal Medicine, Early Online, 1-3 (2010).
Lee et al., *Intra-amniotic inflammation in patients with a positive Amnisure test in preterm labor and intact membranes*, Am J Obstet Gynecol., Supplement to Jan. 2011, 524 S209.
Lee et al., *Measurement of Placental Alpha-Microglobulin-1 in Cervicovaginal Discharge to Diagnose Rupture of Membranes*, Obstetrics & Gynecology, 109(3):634-640 (2007).
Lee et al., *The clinical significance of a positive Amnisure test in women with preterm labor and intact membranes*, J Matern Fetal Neonatal Med., 25(9):1690-1698 (Sep. 2012).

(56) References Cited

OTHER PUBLICATIONS

Lee, M. S., et al., *The clinical significance of a positive Amnisure test™ in women with term, labor with intact membranes*, Journal of Maternal-Fetal and Neonatal Medicine, 22(4):305-310 (2009).

Lee et al., *Insulin-Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF-I and IGF-II Receptors*, Molecular Endocrinology, 2(5):404-411 (1988).

Letter from Drs. Boris B. Fuks, M.D., Ph.D. and Alexander B. Konstantinov, Ph.D. to European Patent Office (signed Jun. 14, 2005), 2 pages.

Letter from Drs. Boris B. Fuks, M.D., Ph.D. and Alexander B. Konstantinov, Ph.D. to European Patent Office (signed Nov. 30, 2005), 1 page.

Lockwood, Charles J. et al., *Fetal Fibronectin in Cervical and Vaginal Secretions as a Predictor of Preterm Delivery*, New England Journal of Medicine 325(10):669-674 (1991).

Lockwood, Charles J. et al., *Fetal membrane rupture is associated with the presence of insulin-like growth factor-binding protein-1 in vaginal secretions*. Am. J. Obstet. Gynecol. 171(1):146-50 (Jul. 1994).

Loukovaara M, et al., *Serum insulin-like growth factor-I and insulin-like growth factor binding protein-3 in premature rupture of membranes*, Acta Obstet Gynecol Scand. 81(10):905-908 (2002) PubMed PMID: 12366479.

Luthman, Holger et al., *Human insulin-like growth-factor-binding protein. Low-molecular-mass form: protein sequence and cDNA cloning*, Eur. J. Biochem. 180:259-265 (1989).

Marcellin, et al., *Comparison of two bedside tests performed on cervicovaginal fluid to diagnose premature rupture of membranes*, J Gynecol Obstet Biol Reprod (Paris) 622:1-6, (2011) [English translation].

Marinaro, Joe A. et al. *O-glycosylation delays the clearance of human IGF-binding protein-6 from the circulation*, European Journal of Endocrinology, 142:512-516 (2000).

Medix Biochemica, *Actim PROM* (product information), (1 page) (2006).

Mercer et al., *The Preterm Prediction Study: prediction of preterm premature rupture of membranes through clinical findings and ancillary testing*, The NICHD Maternal-Fetal Medicine Units Network. Am J Obstet Gynecol, 183:738-745 (2000).

Mercer B M, *Preterm Premature rupture of the membranes*, Obstet Gynecol, 101:178-193 (2003).

Mittal et al., *A role for placental alpha-microglobulin-1 in the identification of women with a sonographic short cervix at risk for spontaneous rupture of membranes*, 528: Am J Obstet Gynecol., S196-S197 Supplement to Dec. 2009.

Morrison et al., *Isolation of transformation-deficient Streptococcus pneumoniae mutants defective in control of competence, using insertion-duplication mutagenesis with the erythromycin resistance determinant of pAM beta 1*, J. Bacteriol., 159(3):870-876 (1984).

Nasimova et al., *Content of PAMG-1, insulin-like growth factor (Somatomedin C) binding protein in sera of diabetic patients*, Bulletin of Experimental Biology and Medicine, 116(9):302-304 (1993) [English abstract on page 303].

Nilsson et al. *Explorative Study of the Protein Composition of Amniotic Fluid by Liquid Chromatography Electrospray Ionization Fourier Transform Ion Cyclotron Resonance Mass Spectrometry*, Journal of Proteome Research, 3(4):884-889 (2004).

Nisell H, et al., *Assessment of fetal fibronectin in cervical secretion in cases of equivocal rupture of the membranes at term*, Acta Obstet Gynecol Scand, 75(2):132-4 (1996).

Ooi, and Herington, *Recognition of insulin-like-growth-factor-binding proteins in serum and amniotic fluid by an antiserum against a low-molecular-mass insulin-like-growth-factor-inhibitor/binding protein*, Biochem. J., 267:615-620 (1990).

Paternoster DM, et al., *Comparative analysis of premature labor markers*, Suppl Acta Bio-Medica de L'Ateneo Parmense 71:331-336 (2000) [English translation Abstract] Italian. PubMed PMID: 11424765.

Pekonen et al. 1989. Auf monoklonalen Antiköipern basierender immunoradiometrischer Assay für insulinähnliches, wachstumsfaktorbindendes Protein / Plazentaprotein 12 mit niedrigem Molekulargewicht (Übersetzung aus dem Englischen). Medix Biochemica. Minerva Institute for Medical Research.

Pekonen, Fredrika et al., *A Monoclonal Antibody-Based Immunoradiometric Assay for Low Molecular Weight Insulin-Like Growth Factor Binding Protein/Placental Protein 12*, Journal of Immunoassay, 10(4):325-337 (1989).

Petrunin et al. 1977. Akush Ginekol (Mosk) 62-64.

Petrunin et al. *The Immunochemical Identification of Organ-Specific α-1 Globulin of the Human Placenta and its Content in the Amniotic Fluid*, Akusherstvo i Ginekologia 1:64-65 (1977) [With English translation].

Petrunin et al., *Isolation and Physiochemical Characteristics of Chorion α-1 Microglobulin*, Bulletin of Experimental Biology and Medicine, 5:558 (1980) (3 pages) [English translation].

Petrunin et al., *regarding PAMG-1*, 369-77 (1990) [English Abstract Only].

Petrunin, D.D. et al., *A Comparative Study of Four Human Placental Proteins in the Course of Pregnancy*, pp. 50-52 (1988) [English abstract on page 52].

Pollet-Villard et al. *Detection of Placental Alpha Microglobulin-1 versus Insulin-Like Growth Factor-Binding Protein-1 in Amniotic Fluid at Term: A Comparative Study*, Amer J Perinatol, 28(6):489-94 (2011).

Povoa, Guilherme, *Cross-reaction of serum somatomedin-binding protein in a radioimmunoassay developed for somatomedin-binding protein isolated from human amniotic fluid*, Acta Endocrinologica, 107:563-570 (1984).

Ragosch, V. et al., *Insulin like growth factor binding protein 1 (IGFBP-1) und fetales Fibronectin in der Diagnostik eines vorzeitigen Blasensprunges*, Geburtsh. u. Frauenheililk. 56:291-296(1996) [English Abstract].

Report on the Nomenclature of the IGF Binding Proteins, Journal of Clinical Endocrinology and Metabolism, 70(3):817-818 (1990).

Request for the Furnishing of Samples of Deposited Microorganisms, to the Russian National Collection of Industrial Microorganisms, for Intl App No. PCT/US2003/025125, dated Sep. 26, 2007 (12 pages).

Rochelson, Burton L. et al., *A Rapid Colorimetric AFP Monoclonal Antibody Tet for the Diagnosis of Preterm Rupture of the Membranes*, Obstetrics & Gynecology 69(2):163-163 (1987).

Rochelson. Burton L. et al., *Rapid Assay—Possible Application in the Diagnosis of Premature Rupture of the Membranes*, Obstetrics & Gynecology, 62(4):414-418 (1983).

Romero et al., *Clinical chorioamnionitis is characterized by changes in the expression of the alarmin HMGB1 and one of its receptors, sRAGE*, J Matern Fetal Neonatal Med., 25(6):558-s567 (2012).

Rosenfeld, Ron. G. et al. *The Insulin-like Growth Factor Binding Protein Superfamily: New Perspectives*, Pediatrics, 104:1018-1021 (1999).

Rutanen, Eeva-Marja et al., *Radioimmunoassay of Placental Protein 12: Levels in Amniotic Fluid, Cord Blood, and Serum of Healthy Adults, Pregnant Women, and Patients with Trophoblastic Disease*, Am. J. Obstet Gynecol., 144(4):460-463 (1982).

Rutanen, Eeva-Marja et al., *Synthesis of Placental Protein 12 by Human Decidua*, Endocrinology, 116(4):1304-1309 (1985).

Rutanen, and Pekonen, *Diagnosis of Premature Rupture of Fetal Membranes by the Measurement of Insulin-like Growth Factor Binding Protein-1 in Cervical Secretion*, Supplement to Am. J. Obstetrics and Gynecology, 164(1) Abstract 38 (Jan. 1991) (3 pages).

Rutanen, E-M, et al., *Evaluation of a rapid strip test for insulin-like growth factor binding protein-1 in the diagnosis of ruptured fetal membranes*. Clinica Chimica Acta 253:91-101 (1996).

(56) References Cited

OTHER PUBLICATIONS

Rutanen, E-M. et al., *Monoclonal Antibodies to the 27-34K Insulin-like Growth Factor Binding Protein*, Biochemical and Biophysical Research Communications 152(1):208-215. (1988).

Rutanen, E-M. et al., *Measurement of insulin-like growth factor binding protein-1 in cervical/vaginal secretions: comparison with the ROM-check Membrane Immunoassay in the diagnosis of ruptured fetal membranes*, Clinica Chimica Acta, 214:73-81 (1993).

Seppälä, M. et al., *Uterine endocrinology and paracrinotogy: insulin-like growth factor binding protein-1 and placental protein 14 revisited*, Human Reproduction, 9(5):917-925 (1994).

Seppala, Markku et al., *Immunologic and Biological Properties and Clinical Significance of Placental Proteins PP5 and PP12*, Annals New York Academy of Sciences, 417:368-382 (1983).

Smith RP, A *Technic for the Detection of Rupture of the Membranes: A Review and Preliminary Report*, Obstet Gynecol., 48:172-176 (1976).

Statement from VTT Technical Research Centre of Finland, *Report of comparison the performance of actim™ Prom test of Medix Biochemica and AmniSure™ test of N-DIA*, Jun. 26, 2003, (1 page).

Supplement to the Expert Opinion in the lawsuit 41 O 331/03, Dec. 11, 2005; (21 pages), [English translation from German].

Tagore, et al., *Comparative analysis of insulin-like growth factor binding protein-1 (IGFBP-1), placental alpha-microglobulln-1 (PAMG-1) and nitrazine test to diagnose premature rupture of membranes in pregnancy*, J. Perinat. Med., 38:1-4 (2010).

Tatarinov, et al., *Placental $\alpha_1$-microglobulin is a protein that binds somatomedins*, pp. 369-378 (1990) [English translation].

Tatarinov, Y.S. et al., *Two New Human Placenta-Specific α-Globulines: Identification, Purification, Characteristics, Cellular Localization and Clinical Investigation*, Scrono Symposium No. 35:35-46, London and New York: Academic Press (1980).

Thomasino et al., *Diagnosing Rupture of Membranes Using Combination Monoclonal/Polyclonal Immunologic Protein Detection*; The Journal of Reproductive Medicine; 58(5-6):187-194 (2013).

Tkachenko and Petrunin, *Immunochemical studies of the system of specific proteins of the human placenta*, Vestn. Ross. Akad. Med. Nauk., 3: 40-44 (1995) (Abstract).

UniProtKB/Swiss-Prot database entry for IGFBP-1 (last accessed on Jan. 28, 2012 at http://www.uniprot.org/uniprot/P08833), (10 pages).

Verhaeghe J, et al., *Regulation of insulin-like growth factor-I and insulin-like growth factor binding protein-1 concentrations in preterm fetuses*, Am J Obstet Gynecol, 188(2):485-91 (2003) PubMed PMID: 12592260.

Voller, A., Maggio, E. T. (ed.), *Heterogeneous Enzyme-Immunoassays and Their Applications*, Enzyme-Immunoassay, 1980 CRC Press, Inc., pp. 181-196 (Chapter 9).

Woltmann, Wiebke et al., *Detection of Ruptured Fetal Membranes using Insulin-like Growth Factor-binding Protein-1*, Z. Geburtsh. Neonatol. 199:243-244 (1995) [English Abstract].

Woytoń J, et al., *Insulin-like growth factor binding protein 1 (IGFBP-1) in vaginal secretion as a marker of premature rupture of amniotic membranes* Ginekol Pol., 70(11):809-14 (1999) Polish. PubMed PMID: 10736957 [With English translation Summary].

Zaraysky, E.I, et al., *Immunoenzyme Assay of Placenta Specific $\alpha_1$-Microglobulin in Donor Blood Serum*, Voprosy Med. Khemii 5:130-132 (1989) [English abstract on p. 132].

Zenobi, et al., *Ion formation in MALDI mass spectrometry*, Mass Spectrom. Rev., 17:337-366 (1998).

Burdett et al, *Proteins of human amniotic fluid. II. Mapping by two-dimensional electrophoresis*, Clinical Chemistry, 28(4):935-940 (Apr. 1982).

Reply to Notice of Opposition filed against EP 2204654, dated Apr. 28, 2014 (81 pages).

Notification to Attend Oral Proceedings in the Opposition filed against EP 2204654, dated Jul. 24, 2014 (19 pages).

EPO Opposition Division's Decision rejecting the Opposition against EP 2204654, dated Mar. 26, 2015 (26 pages).

Petrunin et al. *Immune chemical identification organ-α1-globulin human placenta and its content in the amniotic fluid*, Akush Ginekol (Mosk) 62-64 (1977) [With English translation].

SIPO—Office Action in corresponding CN Application No. 201380074274.9, dated Mar. 10, 2016 (12 pages).

Crowe, C., "AmniSure; (placental alpha-1 microglobulin) Rupture of Fetal Membrane Test", http://webserver.pa-ucl.com/wwwdocs/analyticalproc/FrameA.htm, Mar. 31, 2012 (3 pages).

Canadian Examiner's Report for Application Serial No. 2,533,915, dated Apr. 3, 2017, 3 pages.

European Office Action for Application No. EP13870051.3, dated Jun. 23, 2017, 8 pages.

Extended European Search Report for Application No. 13870051.3 dated Oct. 12, 2016, 9 pages.

Japanese Office Action in International Application No. JP2015-551719, dated Oct. 19, 2017, 4 pages (with English Translation).

\* cited by examiner

METHODS FOR PREDICTING TIME-TO-DELIVERY IN PREGNANT WOMEN

RELATED APPLICATIONS

The present application is a divisional and claims the benefit of U.S. patent application Ser. No. 14/138,753, filed Dec. 23, 2013, which claims the benefit of U.S. Provisional Patent Application Ser. Nos. 61/748,310, filed Jan. 2, 2013, and 61/909,238, filed Nov. 26, 2013. The contents of all of the prior applications are incorporated herein by reference in their entirety.

FIELD OF THE INVENTION

The present disclosure relates to methods for predicting time-to-delivery (TTD) in pregnant patients and/or for determining a patient's risk of preterm labor and/or spontaneous rupture of the chorioamniotic membrane.

BACKGROUND OF THE INVENTION

Prediction of time-to-delivery (TTD) is clinically important among pregnancies at risk for preterm delivery, particularly in regard to administration of corticosteroids (which have optimal benefit within 24 hours to 7 days of administration). In addition, patients at high risk for preterm birth should deliver in a tertiary care unit. Obstetricians are tasked with predicting TTD in patients at risk for preterm delivery, particularly given the controversy over the use of repeated steroids.

The American College of Obstetricians and Gynecologists (ACOG) indicates in its most recent Practice Bulletin on the Management of Preterm Labor that, while many tests to identify women at risk of preterm birth have been proposed and evaluated, only ultrasonography (to determine cervical length) and fetal fibronectin testing have been shown to have benefit. Ultrasonography or fetal fibronectin testing, or a combination of both, may be useful in identifying women who are at high risk for preterm delivery. However, their clinical usefulness may rest primarily with their ability to identify women who are least likely to deliver (i.e., the tests' negative predictive value (NPV)), not women who are most likely to delivery (i.e., a test with a high positive predictive value (PPV)). Thus, there is an urgent need for a test with a high PPV in order to accurately predict imminent delivery, and to allow for salutary intervention.

SUMMARY OF THE INVENTION

As discussed above, what is needed in the art are improved devices and methods for the accurate diagnosis of patients at risk for imminent delivery (e.g., within 14 days, 7 days, or 48 hours), particularly in patients presenting with signs, symptoms or complaints suggestive of preterm labor (PTL), but having no clinical evidence of rupture of fetal membranes (ROM). Such improved devices and methods are of significant value to healthcare providers in deciding how to manage their patients, e.g., in determining whether to administer tocolytics in order to prolong gestation, corticosteroids to improve respiratory development of the fetus, administration of antibiotics to decrease the risk of infection (intra-partum and post-partum), prescription of bed rest, and/or increased observation and fetal monitoring.

Thus, in certain aspects, the present disclosure provides a method of predicting time to delivery (TTD), that includes (e.g., comprises, consists essentially of, consists of): (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) detecting the presence of the PAMG-1/monoclonal antibody complex in the sample only when the concentration of PAMG-1 in the sample exceeds a predefined detection threshold; and (c) predicting that the pregnant woman will deliver within a predetermined time frame if PAMG-1 is detected. In another aspect, the method of predicting TTD includes (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) detecting the presence of the PAMG-1/monoclonal antibody complex in the sample only when the concentration of PAMG-1 in the sample exceeds a predefined detection threshold; and (c) predicting that the pregnant woman will deliver within a predetermined time frame if PAMG-1 is detected; or (d) predicting that the pregnant woman will not deliver within the predetermined time frame if PAMG-1 is not detected. In some embodiments, step (d) comprises predicting that the pregnant woman will not deliver within the predetermined time frame at the time when the vaginal fluid sample was obtained from the pregnant woman. The predetermined time frame for predicting TTD can be, e.g., within about 48 hours; within about 7 days; and/or (iii) within about 14 days. In certain aspects, the method of predicting TTD has one or more of the following positive predictive values (PPVs): (i) at least about 39% for predicting TTD within 48 hours; (ii) at least about 64% for predicting TTD within 7 days; and (iii) at least about 77% for predicting TTD within about 14 days. In certain aspects, the method for predicting TTD has one or more of the following PPVs: (i) about 45.5% for predicting TTD within about 48 hours; (ii) about 81.8% for predicting TTD within about 7 days; and (iii) about 90.9% for predicting TTD within 14 days. In some aspects, the method has a negative predictive value (NPV) of greater than about 90%. In certain aspects, the method for predicting TTD has one or more of the following PPVs: (i) about 45.5% for predicting TTD within 48 hours; and/or (ii) about 78.3% (e.g., about 78%) for predicting TTD within 7 days; and/or (iii) about 87% for predicting TTD within 14 days. In some aspects, the method has a negative predictive value (NPV) of 87% or greater. In still other aspects, the method has one or more of the following NPVs: (i) about 100% for predicting TTD within 48 hours; and/or (ii) about 97.4% (e.g., about 87%) for predicting TTD within 7 days; and/or (iii) about 93.6% (e.g., about 84%) for predicting TTD within 14 days.

In other aspects, the present disclosure provides a method for determining the risk of preterm delivery, wherein the method includes (e.g., comprises, consists essentially of, consists of): (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) detecting the presence of the PAMG-1/monoclonal antibody complex in the sample only when the concentration of PAMG-1 in the sample exceeds a predefined detection threshold; and (c) predicting that the pregnant woman is at risk of preterm delivery if PAMG-1 is detected. In other aspects, the present disclosure provides a method for determining the risk of preterm delivery, wherein the method includes (e.g., comprises, consists essentially of, consists of): (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) detecting the presence of the PAMG-1/monoclonal antibody complex in the sample only when the concentration of PAMG-1 in the sample exceeds a predefined detection threshold; and (c) predicting that the pregnant woman is at risk of preterm delivery if PAMG-1 is detected; or (d) predicting that the pregnant woman is not at risk of preterm delivery if PAMG-1 is not detected. In some embodiments, step (d) comprises predicting that the pregnant woman is not at risk of preterm delivery at the time when the vaginal fluid sample was obtained from the pregnant woman.

In still other aspects, the present disclosure provides a method for determining a pregnant woman's risk of spontaneous rupture of the chorioamniotic membranes, wherein the method includes (e.g., comprises, consists essentially of, consists of): (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) detecting the presence of the PAMG-1/monoclonal antibody complex in the sample only when the concentration of PAMG-1 in the sample exceeds a predefined detection threshold; and (c) determining that the pregnant woman is at risk of spontaneous rupture of the chorioamniotic membranes if PAMG-1 is detected. In another aspect, the present disclosure provides a method for determining a pregnant woman's risk of spontaneous rupture of the chorioamniotic membranes, wherein the method includes: (a) contacting a vaginal fluid sample obtained from a pregnant woman with at least two PAMG-1-specific monoclonal antibodies, wherein at least one of the antibodies binds to PAMG-1 when present in the sample to form a PAMG-1/monoclonal antibody complex; (b) detecting the presence of the PAMG-1/monoclonal antibody complex in the sample only when the concentration of PAMG-1 in the sample exceeds a predefined detection threshold; and (c) determining that the pregnant woman is at risk of spontaneous rupture of the chorioamniotic membranes if PAMG-1 is detected; or (d) determining that the pregnant woman is not at risk of spontaneous rupture of the chorioamniotic membranes if PAMG-1 is not detected. In some embodiments, step (d) comprises predicting that the pregnant woman is not at risk of spontaneous rupture of the chorioamniotic membranes at the time when the vaginal fluid sample was obtained from the pregnant woman.

In certain aspects, the method is for determining the risk of spontaneous preterm premature rupture of the chorioamniotic membranes.

In another aspect, provided herein is a method for ruling out (predicting as highly unlikely) spontaneous preterm premature ROM or preterm delivery by a pregnant woman within a predetermined time frame. The method can include: (a) contacting a vaginal fluid sample obtained from a pregnant woman suspected to be at risk for preterm delivery with at least two PAMG-1-specific monoclonal antibodies, wherein at least one of the antibodies binds to PAMG-1 when present in the sample to form a PAMG-1/monoclonal antibody complex; (b) detecting the presence of any PAMG-1/monoclonal antibody complex present in the sample only when the concentration of PAMG-1 in the sample exceeds a predefined detection threshold; and (c) ruling out (predicting as highly unlikely) spontaneous preterm premature ROM or preterm delivery within the predetermined time frame if PAMG-1 is not detected. The predetermined time frame can be, e.g., within about 48 hours; within about 7 days; and/or (iii) within about 14 days. In some aspects, the method for ruling out (predicting as highly unlikely) spontaneous preterm premature ROM or preterm delivery has a negative predictive value (NPV) of greater than about 90%. In some aspects, the method for ruling out (predicting as highly unlikely) spontaneous preterm premature ROM or preterm delivery has a negative predictive value (NPV) of 87% or greater. In still other aspects, the method has one or more of the following NPVs: (i) about 100% for ruling out (predicting as highly unlikely) spontaneous preterm premature ROM or preterm delivery within 48 hours; and/or (ii) about 97.4% (e.g., about 87%) for ruling out (predicting as highly unlikely) spontaneous preterm premature ROM or preterm delivery within 7 days; and/or (iii) about 93.6% (e.g., about 84%) for ruling out (predicting as highly unlikely) spontaneous preterm premature ROM or preterm delivery within 14 days.

In any of the aspects disclosed above, the method can further include determining that the fetal membranes of the pregnant woman are intact. The method can also include selecting the pregnant woman for analysis by the method only if the pregnant woman presents with one or more, two or more, three or more, or all four of the following: (i) signs, symptoms or complaints suggestive of preterm labor; (ii) a gestational age between 20 weeks and 36 weeks, 6 days; (iii) a cervical length of 25 mm or more; and (iv) a cervical dilatation of 3 cm or less. The method can also include collecting the vaginal fluid sample from the pregnant woman with a collection device (e.g., a flocked swab). In certain aspects, the flocked vaginal swab provides a 1:4 dilution of any PAMG-1 present in the vaginal fluid sample. In certain aspects, the flocked swab provides a dilution of any PAMG-1 present in the vaginal fluid sample in a range of 1:1 to 1:10. The method can also include any one or more of the following steps: contacting the collection device with a solvent to release the collected vaginal fluid sample; collecting the vaginal fluid sample over a time period of about 30 seconds; contacting the collection device with the solvent for about 30 seconds after collecting the vaginal fluid sample; contacting the vaginal fluid sample with the at least two PAMG-1-specific monoclonal antibodies for 5 minutes.

In any of the above aspects, the predetermined detection threshold level of PAMG-1 can be 4 ng/ml.

In any of the above aspects, the at least two PAMG-1 specific monoclonal antibodies can be used in a lateral flow device. The lateral flow device can include a pad region and a test region. The pad region of the test device can include one of the at least two PAMG-1 specific monoclonal antibodies and the test region can include the other of the two. In certain aspects, the PAMG-1 specific monoclonal antibody in the pad region is mobilizable and the PAMG-1 specific monoclonal antibody in the test region is immobilized. In some aspects, the test region of the test device further includes a control region. In some aspects, each of the at least two PAMG-1-specific monoclonal antibodies is an antibody selected from the group consisting of M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94.

In any of the above aspects, the mobilizable antibody in the pad region can be M271, produced by hybridoma N271, deposited with the Russian National Collection of Industrial Microorganisms (VKPM) Depository and assigned accession number VKPM-93, and the immobilized antibody in the test region can be M52, produced by hybridoma N52, deposited with the VKPM and assigned accession number VKPM-92.

In certain of the above methods employing a device, the device can be the device illustrated in FIGS. 1 and 2.

In certain aspects, the present disclosure provides a kit that includes (e.g., comprises, consists essentially of, consists of): (a) a device for detecting the presence of PAMG-1 in a vaginal fluid sample when present at a level above a predetermined threshold; and a vaginal swab. In some aspects, the vaginal swab can be flocked. In some aspects, the kit further includes a vial and/or instructions for use. In certain aspects, the predetermined threshold is 4 ng/ml. In yet other aspects, the device includes a first and a second monoclonal antibody specific for PAMG-1. The first and second PAMG-1-specific monoclonal antibodies can have different binding specificities and affinities for PAMG-1. In some aspects, each of the first and second PAMG-1-specific monoclonal antibodies can be an antibody selected from the group consisting of M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94. In yet other aspects, the test device is a lateral flow device. The test device can include a pad region and a test region. The pad region of the test device can include one of the first and second PAMG-1-specific monoclonal antibodies and the test region can include the other of the first and second PAMG-1-specific monoclonal antibodies. In certain aspects, either or both of the pad and test regions can contain additional PAMG-1-specific monoclonal antibodies and/or mixtures of the first two PAMG-1-specific monoclonal antibodies. In certain aspects, the PAMG-1-specific monoclonal antibody in the pad region can be mobilizable and the PAMG-1-specific monoclonal antibody in the test region can be immobilized. In still other aspects, the mobilizable antibody in the pad region is M271, produced by hybridoma N271, deposited with the Russian National Collection of Industrial Microorganisms (VKPM) Depository and assigned accession number VKPM-93, and the immobilized antibody in the test region is M52, produced by hybridoma N52, deposited with the VKPM and assigned accession number VKPM-92. In some aspects, the test region of the test device further includes a control region. In certain aspects, the kit can be for use in a method of predicting TTD. In other aspects, the kit can be for use in a method of predicting risk of preterm delivery. In still other aspects, the kit can be for use in a method of determining a pregnant woman's risk of spontaneous rupture of the chorioamniotic membranes (ROM) (e.g., preterm premature ROM). In some aspects, the device in the kit is the device illustrated in FIGS. 1 and 2.

Definitions:

As used herein, "time to delivery (TTD)," is the total length of time (e.g., hours, days, weeks) starting from a predetermined beginning time point (e.g., the time a patient presents with potential signs of preterm labor) until a pregnant patient delivers her baby. TTD can be specified to be "within a predetermined time frame," such as, e.g., within about 14 days (or within about 7 days, or within about 48 hours) from the time the prediction is made. As used herein, "predicting TTD" means determining the likelihood of delivery within a predetermined time frame (e.g., within 2, 7, or 14 days. In certain aspects, predicting TTD includes determining that spontaneous preterm premature ROM or preterm delivery within the predetermined time point is highly likely. In certain aspects, predicting TTD includes ruling out spontaneous preterm premature ROM or preterm delivery within the predetermined time point (i.e., determining spontaneous preterm premature ROM or preterm delivery within the predetermined time frame is highly unlikely).

As used herein, "preterm delivery" is defined as delivery before 37 weeks gestational age.

As used herein, a pregnant woman who is determined to be "at risk of preterm delivery" is one presenting with signs, symptoms, or complaints suggestive of preterm labor."

As used herein, a "predefined detection threshold" for a test disclosed herein, is the level (e.g., concentration or amount) at or above which a polypeptide or other substance must be present in a sample (e.g., an undiluted vaginal or cervico-vaginal fluid sample) in order to be detected (i.e., to give a positive result in a test disclosed herein (e.g., TTD test)).

As used herein, the term "antibody" refers to any polypeptide having a binding affinity for an antigen (e.g., PAMG-1) as specified herein, independent of the method used to obtain the polypeptide. For example, the polypeptide may be a monoclonal antibody or fragment thereof, polyclonal antibody or antigen-binding fragment thereof, or any molecule having a binding specificity for a target antigen, as specified herein.

An "antigen" is an entity (e.g., a proteinaceous entity or peptide) to which a binding molecule specifically binds.

The term "epitope" or "antigenic determinant" refers to a site on an antigen to which a binding molecule (e.g., antibody) specifically binds.

As used herein, an antibody that is "specific for" an antigen (e.g., PAMG-1) binds to that antigen.

As used herein, a pregnant woman is "suitable for" or "in need of" predicting TTD according to the methods disclosed herein if she meets predefined criteria, as disclosed herein, such as, but not limited to, having signs, symptoms or complaints suggestive of labor but does not have clinically detectable rupture of membranes (ROM) (e.g., leakage of fluid from cervical os, pooling of fluid in the posterior fornix).

The term "about" as used herein means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Unless otherwise defined, all technical and scientific terms used herein have the same meaning as commonly understood by one of ordinary skill in the art to which this disclosure pertains. In case of conflict, the present document, including definitions, will control.

All publications, patent applications, patents, and other references mentioned herein are incorporated by reference in their entirety. The materials, methods, and examples disclosed herein are illustrative only and not intended to be limiting.

The details of one or more embodiments of the present disclosure are set forth in the accompanying drawings and the description below. Preferred methods and materials are described below, although methods and materials similar or equivalent to those described herein can also be used in the practice or testing of the present disclosure. Other features, objects, and advantages of the methods disclosed herein will be apparent from the description and drawings, and from the claims.

DETAILED DESCRIPTION OF THE INVENTION

Figure 1:
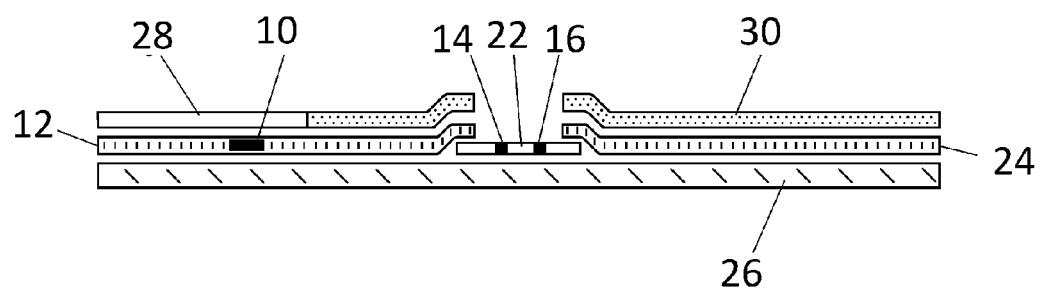
FIG. 1 is a schematic longitudinal sectional view and FIG. 2 is a planar view of an exemplary device that can be used to detect the presence of PAMG-1 in a vaginal fluid sample (e.g., for diagnosing time to delivery (TTD)). The numbers identify the following components of the exemplary device: 10¬M271 antibody region; 12—pad; 14—test region; 16—control region; 18—arrows; 22—nitrocellulose membrane; 24—filter paper membrane; 26—adhesive rigid plastic base; 28—partially transparent protective film with arrows; and 30—non-transparent protective film.

Various aspects of the disclosure are described below.
Overview

The present disclosure provides improved methods for predicting TTD within a predetermined time frame (e.g., within about 14 days, 7 days or 48 hours). Also provided are methods for determining the risk of preterm delivery (i.e., delivery before 37 weeks gestational age), and methods for determining a pregnant woman's risk of spontaneous rupture of chorioamniotic membranes (ROM). In general, the methods disclosed herein include detecting the presence of PAMG-1 when present at a level above a predefined detection threshold. The presently disclosed methods can predict TTD and/or rule out spontaneous preterm delivery with a high PPV and a high NPV. A positive test according to the methods disclosed herein can indicate that delivery is imminent (i.e., within about 14 days, 7 days, or 48 hours). A negative test (absence of detection of PAMG-1) indicates that delivery is not likely to occur within 14 days, 7 days, or 48 hours. A positive test can also indicate that a pregnant woman is at risk of spontaneous preterm premature ROM and/or preterm delivery, while a negative test indicates that a pregnant woman is not at risk of spontaneous preterm premature ROM or preterm delivery. Thus, also provided are methods for ruling out (predicting as highly unlikely) spontaneous preterm premature ROM or preterm delivery.

PAMG-1 is a protein found in high concentrations in amniotic fluid but very low concentrations in background levels of cervico-vaginal discharge. In recent years, the medical community has increasingly accepted the widespread use of detecting PAMG-1 to aid the provider in confirming or ruling out rupture of fetal membranes (ROM). The test used is commercially marketed as the AmniSure® ROM Test, manufactured by AmniSure® International, LLC, Boston, Mass., USA. In a previous investigation of the utility of PAMG-1 for the detection of ROM, it was noted that in 20 out of the 23 cases where the AmniSure® ROM Test was positive and standard clinical assessment (i.e., nitrazine, ferning and pooling) was negative, the patient was ultimately determined to have been ruptured upon retrospective analysis of her clinical course (see, Lee S E, et al. *Obstet Gynecol* 2007; 109:634-640). It was later reported that for all of the preterm patients in the group that showed signs and symptoms of labor, delivery followed within 7 days (see, Lee S M, et al. *J Matern Fetal Neonatal Med* 2009; 22:305-310). The clinical value of a positive AmniSure® ROM Test in the patient presenting with signs and symptoms of preterm labor (PTL) but without ROM was also investigated. The results demonstrated that the AmniSure® ROM Test was predictive of delivery of these patients within 48 hours, 7 days and 14 days (see, Lee M S, et al. *J Matern Fetal Neonatal Med.* 2012 Sep.; 25(9):1690-8), but the PPV was not optimal.

While not intending to be bound by any one particular theory or mechanism of action, the present methods are believed to provide superior performance such as, e.g., PPV and NPV, as well as sensitivity (SN) and specificity (SP), at least in part, by providing a diagnostic test that has an increased sensitivity for detecting PAMG-1 in vaginal secretion samples compared to certain currently available diagnostic methods. For example, while currently available tests that detect PAMG-1 utilize a detection threshold of 5 ng/ml, it is presently discovered that adjusting the detection threshold to 4 ng/ml provides a surprisingly improved diagnostic test (e.g., high PPV and high NPV). It was unexpected that the 4 ng/ml detection threshold could be used in a method for predicting TTD with a high PPV, as presently disclosed, since it was expected that decreasing the detection threshold below 5 ng/ml would increase the frequency of false positive results, thereby decreasing the PPV of the test. Moreover, it was not previously realized that detecting concentrations of PAMG-1 below 5 ng/ml could be useful for predicting TTD, as such small concentrations were thought to be of little clinical significance.

It is also presently discovered that the ideal gestational age of a pregnant woman suitable for predicting TTD according to the methods disclosed herein is specifically between 20 weeks and 36 weeks, 6 days, in order to ensure the highest degree of accuracy of the diagnostic method. Also, in certain embodiments, the TTD test disclosed herein has a high NPV and high PPV, as well as high SN and SP, for the patient population having cervical dilatation of 3 cm or less.

In certain embodiments, a pregnant woman is suitable for and/or selected for predicting TTD if she has a gestational age between 20 weeks and 36 weeks, 6 days. In certain embodiments, a pregnant woman is suitable for and/or selected for predicting TTD if she has a cervical length of 25 mm or more and/or cervical dilatation of 3 cm or less.

In diagnostic testing, the PPV, or precision rate, is the proportion of positive test results that are true positives (such as correct diagnoses). It is a critical measure of the performance of a diagnostic method, as it reflects the probability that a positive test reflects the underlying condition that is being tested for. Other important measures include negative predictive value (NPV), sensitivity (SN), and specificity (SP). NPV indicates the proportion of subjects with a negative test result who are correctly identified as not having the condition being tested. A high NPV for a given test indicates that when the test yields a negative result, it is most likely correct in its assessment, and produces only rarely a false negative result. Thus, for predicting imminent delivery (e.g., within a specific time frame), a high NPV means that the test only rarely predicts that delivery is not imminent when, in reality, it is. The number of true positive results and true negative results that a diagnostic test yields (e.g., in a clinical study), can also be combined to determine the sensitivity (SN) and specificity (SP) of a diagnostic test.

PPV can be calculated according to the following formula:

$$PPV = \frac{\text{number of true positives}}{\text{number of true positives} + \text{number of false positives}}$$

NPV can be calculated according to the following formula:

$$NPV = \frac{\text{number of true negatives}}{\text{number of true negatives} + \text{number of false negatives}}$$

SN can be calculated according to the following formula:

$$SN = \frac{\text{number of true positives}}{\text{number of true positives} + \text{number of false negatives}}$$

SP can be calculated according to the following formula:

$$SP = \frac{\text{number of true negatives}}{\text{number of true negatives} + \text{number of false positives}}$$

In certain aspects, the methods disclosed herein have a PPV of at least about 77% for predicting TTD within 14 days. In a specific embodiment, the PPV for predicting TTD within about 14 days is about 90.9% (e.g., about 91%). In another specific embodiment, the PPV for predicting TTD within about 14 days is about 87%. It is to be appreciated that the present methods also encompass methods for predicting TTD within about 14 days that have a PPV of at least about, e.g., 75%, 76%, 78%, 79%, 80%, 81%, 82%, 83%, 84% 85%, 86%, 87%, 88%, 89%, 90%, 91%, 92%, 93%, 94%, 95%, 96%, 97%, 98%, 99% or 100%. In certain aspects, the PPV for predicting TTD within about 14 days is in the range of about 70%-100%, about 80-%-100%, about 85%-100%, or about 90%-100%.

The methods disclosed herein have a PPV of at least about 64% for predicting TTD within about 7 days. In a specific embodiment, the PPV for predicting TTD within about 7 days is 81.8%. In another specific embodiment, the PPV for predicting TTD within about 7 days is about 78.3% (e.g., about 78%). It is to be appreciated that the present methods also encompass methods for predicting TTD within about 7 days that have a PPV of at least about, e.g., 65%, 66%, 67%, 68%, 69%, 70%, 71%, 72%, 73%, 74%, 75%, 76%, 78%, 79%, 80%, 81%, 82%, 83%, 84% 85%, 86%, 87%, 88%, 89%, 90%, 91%, 92%, 93%, 94%, 95%, 96%, 97%, 98%, 99% or 100%. In certain aspects, the PPV for predicting TTD within 7 days is in the range of about 60%-100%, about 65%-100%, about 70%-100%, about 75%-100%, or about 80%-100%.

In other aspects, the methods disclosed herein have a PPV of for predicting TTD within about 48 hours of at least about 39%. In a specific embodiment, the PPV for predicting TTD within about 48 hours is 45.5%. It is to be appreciated that the present methods also encompass methods for predicting TTD within about 48 hours that have a PPV of at least about, e.g., 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84% 85%, 86%, 87%, 88%, 89%, 90%, 91%, 92%, 93%, 94%, 95%, 96%, 97%, 98%, 99% or 100%. In certain aspects, the PPV for predicting TTD within about 48 hours using the present methods is in the range of about 39%-100%, about 40%-100%, or about 45-100%.

In certain aspects, the NPV for predicting TTD according to the method disclosed herein is at least about 90% (e.g., about 90%, 91%, 92%, 93%, 94%, 95%, 96%, 97%, 98%, 99% or 100%) for predicting TTD within about 48 hours, 7 days or 14 days.

In certain aspects, the SN for predicting TTD according to the method disclosed herein is at least about 70% (e.g., at least about 70%, 71%, 72%, 73%, 74%, 75%, 76%, 77%, 78%, 79%, 80%, 81%, 82%, 83%, 84% 85%, 86%, 87%, 88%, 89%, 90%, 91%, 92%, 93%, 94%, 95%, 96%, 97%, 98%, 99% or 100%) for predicting TTD within about 48 hours, 7 days or 14 days.

In certain aspects, the SP for predicting TTD according to the method disclosed herein is at least about 70% (e.g., at least about 70%, 71%, 72%, 73%, 74%, 75%, 76%, 77%, 78%, 79%, 80%, 81%, 82%, 83%, 84% 85%, 86%, 87%, 88%, 89%, 90%, 91%, 92%, 93%, 94%, 95%, 96%, 97%, 98%, 99% or 100%) for predicting TTD within about 48 hours, 7 days or 14 days.

In certain embodiments, the present methods provide a diagnostic test that has a PPV of about 90.9%, and/or a NPV of about 93.6%, and/or an SN of about 80%, and/or a SP of about 97.3% for predicting TTD within about 14 days. In certain embodiments, the present methods provide a diagnostic test that has a PPV of about 91%, and/or a NPV of about 94%, and/or an SN of about 80%, and/or a SP of about 97.3% for predicting TTD within about 14 days.

In certain embodiments, the present methods provide a diagnostic test that has a PPV of about 87%, a NPV of about 93.6%, an SN of about 80%, and a SP of about 96.1% for predicting TTD within about 14 days. In certain embodiments, the present methods provide a diagnostic test that has a PPV of about 87%, and/or a NPV of about 94%, and/or an SN of about 80%, and/or a SP of about 96% for predicting TTD within about 14 days.

In certain embodiments, the present methods provide a diagnostic test that has a PPV of 81.8%, a NPV of 97.4%, a SN of 90%, and a SP of 95%, for predicting TTD within about 7 days.

In certain embodiments, the present methods provide a diagnostic test that has a PPV of about 78.3%, and/or a NPV of about 97.4%, and/or a SN of about 90%, and/or a SP of about 93.8%, for predicting TTD within about 7 days. In certain embodiments, the present methods provide a diagnostic test that has a PPV of about 78%, and/or a NPV of about 97%, and/or a SN of about 90%, and/or a SP of about 94%, for predicting TTD within about 7 days.

In certain embodiments, the present methods provide a diagnostic test that has a PPV of about 45.5%, a NPV of about 100%, a SN of about 100%, and a SP of about 86.7%, for predicting TTD within about 48 hours.

It is to be understood that the above values and ranges can be adjusted to include confidence intervals (e.g., 95% confidence intervals), as shown, e.g., in Example 2, Tables 2 and 4, below.

The methods disclosed herein are also useful for determining a patient's (i.e., pregnant woman's) risk of preterm delivery. Preterm delivery is defined herein as delivery before 37 weeks gestational age. A positive test obtained according to the methods disclosed herein (i.e., detection of PAMG-1 at a level at or above a predefined detection threshold in a vaginal fluid sample) indicates that a patient is at risk of preterm delivery. In certain embodiments, a patient is selected for testing for risk of preterm delivery if the patient presents with one or more of the following signs: (i) a gestational age between 20 weeks and 36 weeks, 6 days; and/or (ii) a cervical length of 25 mm or more; and/or (iii) a cervical dilatation of 3 cm or less.

The methods disclosed herein are also useful for determining a pregnant woman's risk of spontaneous rupture of the chorioamniotic membranes (ROM), such as, e.g., preterm premature ROM. Spontaneous ROM typically occurs as part of the normal labor process. However, preterm premature ROM (e.g., before reaching 37 weeks gestational age) can also occur. It is advantageous to be able to determine a patient's risk of spontaneous ROM, including preterm premature ROM, so that appropriate intervening measures (e.g., administration of tocolytics in order to prolong gestation, corticosteroids to improve respiratory development of the fetus, administration of antibiotics to decrease the risk of infection (intra-partum and post-partum), prescription of bed rest, and/or increased observation and fetal monitoring) can be taken, if necessary. In certain embodiments, a patient is selected for testing for risk of spontaneous ROM if the patient presents with one or more of the following signs: (i) a gestational age between 20 weeks and 36 weeks, 6 days; and/or (ii) a cervical length of 25 mm or more; and/or (iii) a cervical dilatation of 3 cm or less.

PAMG-1

PAMG-1 was isolated in 1977 from amniotic fluid by D. Petrunin and was originally referred to as specific alpha-1 globulin of placenta (D. Petrunin, et al., "Immunological Identification of Organ Specific alpha-1 Globulin of Human Placenta and Its Content in the Amniotic Fluid," in Akusherstvo i Ginekologiya, 1977, N 1, pp. 64-65, Moscow, USSR).

The exemplary steps of the isolation of PAMG-1 from amniotic fluid of pregnant women are outlined in Table 1, and discussed, below. It is to be understood, however, that PAMG-1 can be isolated according to any suitable method known in the art, from any suitable source.

TABLE 1

Exemplary Steps of Isolation of PAMG-1

| Steps of Isolation | Purity (%) | Yield (%) |
|---|---|---|
| Amniotic fluid 16-25 weeks pregnancy | 4 | 100 |
| Precipitation by 0.5% lanthanum chloride | 25 | 90 |
| Precipitation by ammonium sulphate at 50% saturation | 35 | 70 |
| Precipitation by lithium sulphate at 60% saturation | 60 | 60 |
| Reverse Phase Chromatography Separation | 90 | 30 |

PAMG-1 was isolated from the amniotic fluid of women at 16 to 25 weeks of gestation. The fluid was obtained from women whose pregnancy was terminated due to medical considerations. A 10% solution of lanthanum chloride was added at the volumetric ratio 20:1 (so that its final concentration was 0.5%) to the amniotic fluid and kept at 4° C. for 18 hours. The precipitate was further separated by centrifugation at 8,000 rpm for 30 minutes. The precipitate was dissolved in a saturated solution of $Na_2HPO_4$ and then the precipitate of insoluble lanthanum salts (produced in the process of centrifugation at 8,000 rpm for 30 minutes) was separated. The resulting solution was fractionated with 50% saturated ammonium sulphate by incubating at 4° C. for 18 hours, and the resulting precipitate was dissolved in distilled water in such a way as to restore the volume of the dissolved precipitation fractions to the initial volume of the amniotic fluid. Then, the solution was precipitated by 60% saturated lithium sulphate, and the precipitate was dissolved in a small amount of distilled water. After dialysis, the admixtures were adsorbed with calcium pyrophosphate by adding an equal volume of moisture absorbent to the protein solution, intermixing and incubating for 10-15 minutes, and separating the absorbent by centrifugation.

The molecular weight of PAMG-1 was first reported as 32 kDa (Boltovskaya, M. N. et al., "Histochemical and Clinico-Diagnostic Study of the Placental Alpha-Microglobulin [PAMG-1] Using Monoclonal Antibodies," in Bulletin of Experimental. Biology and Medicine, 1991, No. 10, pp. 397-400); however, it is generally accepted now that PAMG-1 has a molecular weight of 34 kDa (see, e.g., Pollet-Villard et al. (Amer J Perinatol 2011 Jun.; 28(6):489-94)). PAMG-1 is a protein that is present in the serum, amniotic fluid and vaginal secretion of pregnant women. PAMG-1 exists in amniotic fluid at a concentration about at least 100 times greater than in the serum of pregnant women and at least 3000 times greater than in vaginal secretions of pregnant women in the absence of fetal membranes rupture. As a result, even when a small amount of amniotic liquid (about 1/100 of one drop per 1 ml of vaginal secretion) is dissolved in a vaginal secretion sample, a sufficient amount of PAMG-1 is present in this vaginal secretion sample to indicate that fetal membrane rupture has taken place. Further, because of the low concentration of PAMG-1 in blood serum, the insignificant admixture of blood serum to the vaginal fluid sample (10-15%) does not affect the results produced by the devices and methods of the present disclosure. Detection of PAMG-1 for the diagnosis of ROM has been shown to be superior to the detection of other amniotic proteins such as, e.g., IGFBP-1, a 28 kDa protein (see, Pollet-Villard et al. (supra) and European Guidelines on preterm labor (The Journal of Maternal-Fetal and Neonatal Medicine, 2011; Early Online, 1-9)).

Because the presence of amniotic fluid in a vaginal secretion can be indicative of a fetal membrane rupture, the detection of the amniotic protein PAMG-1 in vaginal secretion can be used to detect fetal membrane rupture. However, it is presently discovered that the methods disclosed herein can be used to detect PAMG-1 in vaginal secretions even in the absence of detectable ROM to accurately predict TTD, by adjusting the detection threshold of PAMG-1 to about 4 ng/ml. While not intending to be bound by theory or limited to any one particular mechanism of action, it is believed that PAMG-1 is transudated through chorioamniotic pores in fetal membranes during uterine contractions that occur when delivery is imminent (i.e., will occur within, e.g., 14 days, 7 days, or 48 hours). Degradation of extracellular matrix of fetal membranes due to inflammatory process of labor and or infection may also lead to the finding of increased levels of PAMG-1 in cervico-vaginal secretions.

PAMG-1 Antibodies

The methods disclosed herein encompass detecting the presence of PAMG-1 protein in vaginal secretion samples obtained from pregnant women. PAMG-1 protein can be detected according to any suitable method known in the art.

An exemplary method for the detection of PAMG-1 in vaginal fluid samples includes, but is not limited to, immunoassay (e.g., ELISA), using, e.g., PAMG-1 specific antibodies (e.g., monoclonal antibodies or antigen-binding fragments thereof) described herein.

PAMG-1 antibodies, as disclosed herein, can detect very low concentrations of PAMG-1. For example, concentration of 0.05 ng/ml PAMG-1 can be detected. Because the maximum concentration of PAMG-1 in serum is about 25 ng/ml, as compared to a minimum concentration of about 1680 ng/ml in amniotic fluid, and because the background concentration of PAMG-1 in vaginal secretions is very low, about 0.2 ng/ml, a lower threshold level for PAMG-1 can be used in the methods of the present disclosure for detecting the occurrence of amniotic fluid in the vagina. It is presently discovered that a predefined threshold of about 4 ng/ml for PAMG-1 can be used in the methods disclosed herein.

As a result, the devices and methods of the present disclosure are not influenced by the presence of vaginitis or other variables, which had a negative impact on the accuracy of prior methods for detecting fetal membrane ruptures. The maximum concentration of PAMG-1 in inflammation exudate is 3 ng/ml (see, e.g., U.S. Pat. No. 7,709,272 by Fuks et al.). The same concentration of PAMG-1 may occur if blood serum admixture to vaginal secretion does not exceed 10-15%. In addition, a large ratio of concentrations serum-to-amniotic PAMG-1 makes the devices and methods of the present disclosure significantly less likely to produce false positive results due to the presence of blood serum in vaginal secretions, even with a low PAMG-1-detection threshold.

The present disclosure provides methods and devices for predicting TTD at a PAMG-1 detection threshold of about 4 ng/ml. The detection threshold can be adjusted by selecting PAMG-1 antibodies (e.g., a pair of PAMG-1 binding antibodies) with specific binding affinities for PAMG-1, such that the combination of the PAMG-1 binding antibodies provides the desired detection threshold. The detection threshold can also be adjusted, e.g., by using at least one or more additional antibodies in test region (e.g., test in FIGS. 1 and 2) against PAMG-1 to adjust the predefined detection threshold (see U.S. Pat. No. 7,709,272 by Fuks et al.), or by adjusting the test procedure, as discussed in detail below.

PAMG-1 polypeptide separated from body fluids, produced recombinantly, or by chemical synthesis, and fragments or other derivatives or analogs thereof, including fusion proteins, may be used as an immunogen to generate antibodies that recognize the PAMG-1 polypeptide. The antibodies disclosed herein can include an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. PAMG-1 antibodies may have both a heavy and a light chain.

Antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, so long as they exhibit the desired activity, e.g., binding to PAMG-1, can be used to perform the methods disclosed herein.

Anti-PAMG-1 antibodies as, e.g., disclosed herein, may recognize PAMG-1 from one or more different mammalian species. Alternatively, an antibody disclosed herein may be specific for a single form of PAMG-1. In certain embodiments, an anti-PAMG-1 antibody is specific for human PAMG-1.

Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, X-ray crystallography and 2-dimensional nuclear magnetic resonance. See, e.g., Epitope Mapping Protocols in Methods in Molecular Biology, Vol. 66, G. E. Morris, Ed. (1996).

Antibodies that recognize the same or overlapping epitopes can be identified in a simple immunoassay showing the ability of one antibody to block the binding of another antibody to a target antigen, i.e., a competitive binding assay. Competitive binding is determined in an assay in which the binding molecule being tested inhibits specific binding of a reference binding molecule to a common antigen, such as PAMG-1. Numerous types of competitive binding assays are known, for example: solid phase direct or indirect radioimmunoassay (RIA); solid phase direct or indirect enzyme immunoassay (EIA) sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using I-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

Typically, such an assay involves the use of purified antigen bound to a solid surface or cells bearing either of these, an unlabeled test binding molecule and a labeled reference binding molecule. Competitive inhibition is measured by determining the amount of label bound to the solid surface or cells in the presence of the test binding molecule. Usually the test binding molecule is present in excess. Usually, when a competing binding molecule is present in excess, it will inhibit specific binding of a reference binding molecule to a common antigen by at least 50-55%, 55-60%, 60-65%, 65-70% 70-75% or more.

Various procedures known in the art may be used for the production of polyclonal antibodies to PAMG-1 polypeptide or derivative or analog thereof. For the production of antibody, various host animals can be immunized by injection with the PAMG-1 polypeptide, or a derivative (e.g., fragment or fusion protein) thereof, including but not limited to rabbits, mice, rats, sheep, goats, etc. In one embodiment, the PAMG-1 polypeptide or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the PAMG-1 polypeptide, or fragment, analog, or derivative thereof, any technique that provides for the production of antibody molecules by continuous cell lines in culture may be used. These include but are not limited to the hybridoma technique originally developed by Kohler and Milstein (Nature 1975, 256:495-497), as well as the trioma technique, the human B-cell hybridoma technique (Kozbor et al., Immunology Today 1983, 4:72; Cote et al., Proc. Natl. Acad. Sci. U.S.A. 1983, 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the present disclosure, monoclonal antibodies can be produced in germ-free animals (International Patent Publication No. WO 89/12690, published 28 Dec. 1989). In fact, according to the present disclosure, techniques developed for the production of "chimeric antibodies" (Morrison et al., J. Bacteriol. 1984, 159:870; Neuberger et al., Nature 1984, 312:604-608; Takeda et al., 1985, Nature 314:452-454) by splicing the genes from a mouse antibody molecule specific for an PAMG-1 polypeptide together with genes from a human antibody molecule of appropriate biological activity can be used; such antibodies are within the scope of this present disclosure. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the present disclosure, techniques described for the production of single chain antibodies (U.S. Pat. Nos. 5,476,786 and 5,132,405 to Huston; U.S. Pat. No. 4,946,778) can be adapted to produce PAMG-1 polypeptide-specific single chain antibodies. Indeed, these genes can be delivered for expression in vivo. An additional embodiment of the disclosure utilizes the techniques described for the construction of Fab expression libraries (Huse et al., Science 1989, 246:1275-1281) to allow rapid and easy identification of monoclonal Fab fragments with the desired specificity for a PAMG-1 polypeptide, or its derivatives, or analogs.

Antibody fragments that contain the idiotype of the antibody molecule can be generated by known techniques. For example, such fragments include but are not limited to: the $F(ab)_2$ fragment which can be produced by pepsin digestion of the antibody molecule; the Fab fragments which can be generated by reducing the disulfide bridges of the $F(ab)_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present disclosure. For example, to select antibodies which recognize a specific epitope of a PAMG-1 polypeptide, one may assay generated hybridomas for a product which binds to a PAMG-1 polypeptide fragment containing such epitope. For selection of an antibody specific to a PAMG-1 polypeptide from a particular species of animal, one can select on the basis of positive binding with PAMG-1 polypeptide expressed by or isolated from cells of that species of animal.

In certain aspects disclosed herein, the PAMG-1-specific monoclonal antibodies disclosed herein can be, e.g., M271, produced by hybridoma N271, deposited with the Russian National Collection of Industrial Microorganisms (VKPM) Depository and assigned accession number VKPM-93; M52, produced by hybridoma N52, deposited with the VKPM and assigned accession number VKPM-92; and M42, produced by hybridoma N42, deposited with the VKPM and assigned accession number VKPM-94. The binding properties and other characteristics of those PAMG-1 specific monoclonal antibodies are disclosed in detail in U.S. Pat. No. 7,709,272 to Fuks et al. Hybridoma cell lines producing, e.g., PAMG-1 specific antibodies, such as those disclosed above, can be produced by the following procedure. First, mice having spleen and lymph node B-cells are immunized with PAMG-1. Hybridomas are then produced to immortalize the B-cells. The B-cells may be spleen and/or lymph node B-cells. Those hybridomas, which produce a monoclonal antibody having a binding affinity for PAMG-1, are then identified in an ELISA: first layer: PAMG-1; second layer: hybridoma supernatant; and third layer: conjugate of rabbit anti-mouse antibodies labeled by horse radish peroxidase. These identified hybridomas are then cultivated in vitro or in ascites and the monoclonal antibodies they produce are isolated.

As disclosed herein, two or more PAMG-1 specific antibodies (e.g., monoclonal antibodies) can be used in combination to detect PAMG-1 in a vaginal fluid sample. In certain embodiments, at least one of the antibodies used in a method disclosed herein is detectably labeled. A variety of detectable markers can be used, including, but not limited to, stained particles, enzymes, fluorescent dyes, and radioactive isotopes. One particular example of a detectable marker is a gold stained particle having an average dimension in the range of 20 to 30 nm. Another example of a detectable marker is horseradish peroxidase. Methods for attaching a detectable marker to an antibody are described, for example, in Methods In Enzymology, 1981, Vol. 73, pp. 3-46 by Harlow, E., and Lane, D.; in "Antibodies a Laboratory Manual," Cold Spring Harbor Laboratory, 1988, pp. 322, 323, and 343; and Pierce Catalog, pp. T9-T17 (1996). Suitable enzymes include, but are not limited to, alkaline phosphatase and horseradish peroxidase. Other markers or labels for use according to the present disclosure include colloidal gold, colored latex beads, magnetic beads, fluorescent labels (e.g., fluorescene isothiocyanate (FITC), phycoerythrin (PE), Texas red (TR), rhodamine, free or chelated lanthanide series salts, especially Eu3+, to name a few fluorophores), chemiluminescent molecules, radio-isotopes ($^{125}$I, $^{32}$P, $^{35}$S, chelated Tc, etc.) or magnetic resonance imaging labels. Other markers include fluorescence quenching and fluorescence transfer markers, e.g., as used in homogenous as well as solid phase assays. Furthermore, in accordance with the present disclosure a marker can be an epitope, binding partner, or "handle" for interaction with another molecule, such as biotin-streptavidin; glutathione- GST; hexahistidine-nickel; etc. The present disclosure also contemplates using secondary antibodies, which are themselves detectably labeled, as markers (e.g., in a situation where the anti-PAMG-1 antibody pair uses antibodies with Fc portions from two different animal species).

The antibodies disclosed herein can be mobilizable (e.g., able to move upon introduction of a fluid sample (e.g., in a flow device) and/or immobilized (e.g., in the test region of a strip device). Methods for immobilizing antibodies are well known in the art.

Detection of PAMG-1

Immunoassays, particularly immunochromatographic assays, constitute a preferred technique in accordance with the present disclosure, and immunoassays are set forth in detail below. These assays have the advantage of specificity, accuracy, speed, and economy. Other methods for detecting and quantitating PAMG-1, however, can also be used. One such technique is mass spectrometry, e.g., using matrix-assisted laser-desorption (MALDI) time-of-flight (TOF) mass spectrometry (MS) with delayed extraction and a reflectron in the time-of-flight chamber. Preferably MALDI assays are performed on silicon arrays. An example of an array for MALDI is 200 µm circular gel pads at 350 µm centers, on oxidized silicon. A hydrophobic surface (repellent surface) between gelpads further provides a more focused matrix/protein spot for MALDI, thereby improving signal for quantitation. For example, spots produced using the Packard Bioscience system can be less than 200 µm in diameter. The Piezo system can deliver about 300 pL of MALDI matrix (e.g., DHB, sinapinic acid) to the exact position of the affinity capture agent-peptide spot to create a homogeneous peptide/matrix crystal. Desorption/Ionization (Karas, et al. Ion Processes, 1987, v. 78, pp. 53-68 or Zenobi, et al. Mass Spectrom. Rev. 1998, v. 17, pp. 337-366) from this crystal in a MALDI-MS (e.g., Perseptive Voyager) yields a mass spectrum where the height of a peptide peak is relative to the amount protein containing that peptide.

An alternative technique for use in the methods disclosed herein is capillary electrophoresis chromatography, which can permit quantitation of an analyte present in a small amount of sample.

Furthermore, quantitative biochemical techniques, such as polyacrylamide gel electrophoresis, high performance liquid chromatography, and the like may be employed, alone or in combination, to detect and quantitate the amount of PAMG-1 in a sample.

Such immunoassays using exemplary PAMG-1 specific antibodies encompassed by the presently disclosed methods are described in detail in U.S. Pat. No. 7,709,272 by Fuks et al.

Immunological Methods and Devices for Detecting PAMG-1

Various means known in the art for detecting immuno-specific binding of an antibody to an antigen can be used to detect the binding in accordance with the present disclosure. An early method of detecting interaction between an antigen and an antibody involved in analysis of the complex is by precipitation in gels. A further method of detecting an analyte-detector antibody binding pair includes the use of radioiodinated detector antibodies or a radioiodinated protein which is reactive with IgG, such as Protein A. These early methods are well known to persons skilled in the art, as reviewed in Methods in Enzymology, 1980, v. 70, pp. 166-198. By selecting an antibody and conditions that yield a positive result above the threshold values for PROM disclosed herein, one may employ this technology in the practice of the methods disclosed herein.

Later methods for determining the presence of an analyte in a sample using only one antibody included competitive binding assays. In this technique the antibody, which most often would be immobilized onto a solid support, would be exposed to a sample suspected of containing the analyte together with a known quantity of labeled analyte. The two analytes, the labeled analyte and the analyte in the sample would then compete for binding sites on the antibody. Either free labeled analyte or bound labeled analyte is determined, and from this measurement the amount of competing analyte in the sample is known. A more complete description of this method is disclosed in "Basic Principles of Antigen-Antibody Reaction", Elvin A. Labat, (Methods in Enzymology, 70, 3-70, 1980). In this example the labeled analyte can be labeled with either a radioisotope or an enzyme label.

More current immunoassays utilize a double antibody method for detecting the presence of an analyte. These techniques are also reviewed in the above referenced volume of Methods in Enzymology. Therefore, according to one embodiment of the present disclosure, the presence of the individual markers is determined using a pair of antibodies for each of the markers to be detected. One of said pairs of antibodies is referred to herein as a "detector antibody" and the other of said pair of antibodies is referred to herein as a "capture antibody". One embodiment of the present disclosure thus uses the double antibody sandwich method for detecting PAMG-1 in a sample of vaginal fluid. In this method, the analyte is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Common early forms of solid supports include plates, tubes or beads of polystyrene, all of which are well known in the field of radioimmunoassay and enzyme immunoassay. More recently, a number of porous materials such as nylon, nitrocellulose, cellulose acetate, glass fibers and other porous polymers have been employed as solid supports.

Thus, in a specific embodiment, the device of the disclosure comprises means for conducting an immunochromatographic assay ("immunochromatographic assay device"). Such a device comprises a solid phase means for conducting a liquid. As used herein, the term "solid phase means for conducting a liquid" refers to a solid support that allows migration of a liquid therethrough, e.g., via capillary action. A typical product of this nature is a nitrocellulose membrane, which may be prepared by methods well known to those skilled in the art.

Many immunochromatographic assay means and formats are known in the art, and can be used in the practice of the methods disclosed herein. Immunochromatographic assays using a membrane as a solid support in a dipstick or flow-through device are well established for use in the clinical laboratory and for alternative, i.e., non-laboratory, site testing. The usual presentation for an immunochromatographic assay device is a membrane (cellulosic or non-cellulosic) enclosed in a plastic holder. The plastic holder keeps the membrane in a suitable configuration in order to ensure correct functioning of the entire device. There are many variations of the basic structure of assay devices. For example, Litman et al. (U.S. Pat. Nos. 5,156,952 and 5,030,558) describe an assay method and device for determining the presence of a minimum amount of an analyte in a sample. Ullman et al. (U.S. Pat. Nos. 5,137,808 and 4,857,453) describe a device to house an assay membrane that includes self-contained liquid reagents to aid sample flow.

Dafforn et al. (U.S. Pat. No. 4,981,768) describes a device with ports for applying sample and extra liquid. Corti et al. (European Patent Application No. 89118378.2), Greenquist et al. (U.S. Pat. No. 4,806,312) and Berger et al. (U.S. Pat. No. 5,114,673) also describe assay devices.

Preferably, the immunochromatographic assay means includes a control to indicate that the assay has proceeded correctly. The control can be a specific binding reactant at a spot more distal from the sample application point on the solid phase support than the detection zone that will bind to labeled reagent in the presence or absence of analyte, thus indicating that the mobilizable receptor has migrated a sufficient distance with the liquid sample to give a meaningful result.

Suitable labels for use in immunochromatographic assays include enzymes, fluorophores, chromophores, radioisotopes, dyes, colloidal gold, colloidal carbon, latex particles, and chemiluminescent agents. When a control marker is employed, the same or different labels may be used for the receptor and control marker.

One embodiment of the present disclosure uses a flow-through type immunoassay device. Valkirs et al. (U.S. Pat. No. 4,632,901) discloses a device comprising antibody, specific to an antigen analyte, bound to a porous membrane or filter to which is added a liquid sample. As the liquid flows through the membrane, target analytes bind to the antibody. The addition of the sample is followed by the addition of a labeled antibody. The visual detection of the labeled antibody provides an indication of the presence of the target analyte in the sample.

Another example of a flow-through device is disclosed by Kromer et al. (EP-A 0 229 359), which describes a reagent delivery system comprising a matrix saturated with a reagent or components thereof dispersed in a water soluble polymer for controlling the dissolution rate of the reagent for delivery to a reaction matrix positioned below the matrix.

In migration type assays, the solid phase support, e.g., membrane, is impregnated with the reagents needed to perform the assay. An analyte detection zone is provided in which labeled analyte is bound and the results of the assay are read. For example, see Tom et al. (U.S. Pat. No. 4,366,241), and Zuk (EP-A 0 143 574). Migration assay devices usually incorporate within them reagents that have been attached to colored labels such as colloidal gold or carbon, thereby permitting visible detection of the assay results without addition of further substances. See for example, Bernstein (U.S. Pat. No. 4,770,853), May et al. (WO 88/08534), and Ching et al. (EP-A 0 299 428). All of these known types of flow-through devices can be used according to the methods disclosed herein.

Direct labels are one example of labels that can be used in immune-chromatographic assays according to the present disclosure. A direct label has been defined as an entity, which in its natural state, is readily visible, either to the naked eye, or with the aid of an optical filter and/or applied stimulation, e.g., U.V. light, to promote fluorescence. Examples of colored labels that can be used according to the present disclosure, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionuclide, a fluorescent moiety or a luminescent moiety. In addition to these direct labeling devices, indirect labels comprising enzymes can also be used according to the present disclosure. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in Methods in Enzymology, 70. 419-439, 1980 and in U.S. Pat. No. 4,857,453.

In a specific embodiment, the diagnostic device of the present disclosure comprises a membrane assembly having a detection section proximal to the point of introduction of the sample, and a capture section downstream from that position. The detector section contains antibodies (detector antibodies) (e.g., monoclonal antibodies), which will react with any analytes of the present disclosure that are present in the sample. The detector antibodies are reversibly immobilized onto the membrane and will migrate with the sample, when in use. It is preferred although not essential, that the detector antibodies are labeled, for example, with a radionuclide, an enzyme, a fluorescent moiety, luminescent moiety or a colored label such as those described in the prior art, and discussed above. Specifically, one could employ a reactive label, so that for example, the antibody would appear gold before capture of the antigen, and would change to purple upon capture.

The capture section which, as stated, is downstream from the detector section, comprises capture antibodies (e.g., monoclonal antibodies), which are irreversibly immobilized onto the solid support, each antibody immobilized at a different position in the capture section. The antibodies and necessary reagents are immobilized onto the solid support using standard art recognized techniques, as discussed in the flow-through type immunoassay devices discussed previously. In general, the antibodies absorbed onto the solid supports as a result of hydrophobic interactions between non-polar protein substructures and non-polar support matrix material.

A particular advantage of the immunochromatographic assay technology of the present disclosure is that it overcomes the inability of these assays to provide quantitative data. Thus, the capture section can contain a mixture of immobilized antibodies specific for PAMG-1, such that a signal is only produced when the amount of PAMG-1 in the sample exceeds the desired detection threshold.

In addition, the present disclosure contemplates use of homogeneous immunoassay formats. One example of such a competitive homogeneous method is found in U.S. Pat. No. 3,817,837 by Rubenstein and Ullman, which describes a technique in which ligand and enzyme-bound-ligand compete for antibody binding sites. Since binding of the antibody to the enzyme-bound-ligand alters its enzymatic activity, the concentration of ligand present can be estimated by measuring the rate at which such a mixture converts substrate to product. Thus, in a homogeneous method, the detectable property of the label is inherently different depending on whether bound or unbound. In its bound state, the label will have greater or lesser signal intensity. Usually, binding of antibody to the labeled ligand causes a decrease in signal intensity, e.g., when the label is an enzyme. Typical products in this category include the EMIT line of enzyme immunoassays from Syva Company and the TDX line of fluorescence polarization immunoassays from Abbott Diagnostics. A particular homogeneous assay could be prepared with the disposition of all of the analytes on beads, in which event the sample would be introduced and the beads thereafter spun down and detected.

Other examples of biological diagnostic devices that can be used according to the present disclosure include the devices described by G. Grenner, P.B. Diagnostics Systems, Inc., in U.S. Pat. Nos. 4,906,439 and 4,918,025. The Grenner '439 device comprises a diagnostic test element and a sample application unit comprising a fluid delivery element that is characterized as having a layer with a plurality of grooves for the delivery of the sample to the test element. Grenner '025 relates to a device that includes a sample introducing means such as a membrane adjacent to which is positioned a capillary containing a fixed reagent and a waste liquid reservoir. Release of the fixed reagent from the capillary completes the reaction after the sample is deposited, and excess liquid is retained by the waste reservoir, so that the device is self-contained.

While the measurement with a membrane is preferred, it is to be understood that other techniques and corresponding sensor devices may likewise be used in similar fashion to the above. There are currently available several types of automated assay apparatus, which can undertake an assay on a number of samples contemporaneously. These automated assay apparatuses include continuous/random access assay apparatus. Examples of such systems include OPUS™ of PB Diagnostic System, Inc. and the IMX™ Analyzer introduced by Abbott Laboratories of North Chicago, Ill. in 1988. In general, a sample of the test fluid is typically provided in a sample cup and all the process steps including pipetting of the sample into the assay test element, incubation and reading of the signal obtained are carried out automatically. The automated assay systems generally include a series of workstations each of which performs one of the steps in the test procedure. The assay element may be transported from one workstation to the next by various means such as a carousel or movable rack to enable the test steps to be accomplished sequentially. The assay elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps, typically a fluorescent or a colorimetric change in the reagents present on the porous member to be read, such as by a means of a spectroscopy or fluorimeter, which are included within the assay system. The automated assay instruments of PB Diagnostic Systems, Inc. are described in U.S. Pat. Nos. 5,051,237; 5,138,868; 5,141,871 and 5,147,609.

Further classes of immunochemical analyzer systems, which can be used in practicing the methods disclosed herein, are the biosensors or optical immunosensor systems. In general an optical biosensor is a device that uses optical principles quantitatively to convert chemical or biochemical concentrations or activities of interest into electrical signals. These systems can be grouped into four major categories: reflection techniques; surface plasmon resonance; fiber optic techniques and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.). Examples of optical immunosensors are described in general in a review article by G. A. Robins (Advances in Biosensors), Vol. 1, pp. 229-256, 1991. More specific descriptions of these devices are found for example in U.S. Pat. Nos. 4,810,658; 4,978,503; and 5,186,897; R. A. Brady et al. (Phil. Trans. R. Soc. Land. B 316, 143-160, 1987) and G. A. Robinson et al. (in Sensors and Actuators, Elsevier, 1992).

The methods and corresponding kits of the present disclosure are capable of incorporation and practice within a variety of optical measurement systems. Specifically, while the kits and materials of the present disclosure may be practiced in an immunoassay format, such format itself is capable of embodiment in a variety of optoelectronic detection systems. More particularly, a variety of optical immunosensor technologies are already known that may be facilitated and implemented in the practice of the methods disclosed herein. Thus, for example, devices and techniques such as reflection techniques, surface plasmon resonance, fiber optic waveguide techniques and integrated optic devices, may all be adopted and specifically configured to detect and display the results of the examination of a patient's biological sample in accordance with the present method. Particular reflection techniques, such as reflectometry and ellipsometry, and the specific use of optical fibers, optical waveguides, fluorescent capillary fill devices and integrated optical biosensors, present but a few of the variant techniques and equipment that may be employed. A general review of these devices may be found in Robinson, G. A., Optical Immunosensors: An Overview, Advances in Biosensors, Vol. 1, pp. 229-256 (1991).

More particularly, ellipsometry relies on the direction of a polarized light beam first against a reference surface (a standard) and thereafter against the sample surface, following which a comparison of the nature and extent of the resulting reflections can be made. Particularly, the binding of analyte to receptor molecules will be measured as a chain the thickness of the surface relative to the reference surface.

In the instance of multiple internal reflection spectroscopy, for example, the ligand and its receptor may be covalently immobilized on the optical surface of a planar, fused-quartz waveguide after which a light beam may be internally reflected within the waveguide and would penetrate into a solution adjacent the waveguide, so that refractive differences would be capable of measurement as between the standard and the sample. In this particular format, a fluorescent label may be associated and measurements of fluorescence resultantly taken to determine the present extent of binding.

An additional technique utilizes the technology known as fluorescent capillary fill device. In this particular technology, two glass plates held apart by a gap of capillary dimension are utilized. Receptor molecules may be immobilized onto the base plate, which also acts as an optical waveguide. Competitive or sandwich assays utilizing FITC labeling may be performed and induced fluorescence is coupled into the waveguide with signal from bound as opposed to unbound sources. Such signal is discriminated by its angular divergence upon exiting the waveguide. Surface Plasmon Resonance (SPR) devices have also been prepared which operate in response to the coupling of light incident upon a thin metal film into surface modes associated with collective electron oscillations within the metal film. Resonance condition is dependent upon the optical characteristics of the metal film, its thickness, the refractive indices of the dielectric on either side of it, and the angle of incidence of light. Receptor molecules are bound to the top side of the metal film, and the light is directed at the bottom side of the film, such as through a prism substrate. The target analyte, when binding to these receptors, will cause a shift in the resonance condition because of the change it produces in the local refractive index. Resonance is observed by a monitoring of the reflected light intensity as the angle of incidence at the light beam on the metal film surface varies. The change in resonance angle will directly correlate with the amount of analyte bound.

The techniques involving fiber optic systems include the evanescent field fluorescence. In this instance, the cladding is removed from the end of an optical fiber, thus producing a sensor element that evanescently interacts with the surrounding medium. Receptor molecules are bound to the exposed fiber surface, and direct assays may be performed utilizing the natural fluorescence of the receptor and conjugate proteins. Competitive or sandwich assays may be performed using FITC labeling to achieve greater sensitivity. In operation, a light wave is coupled into the fiber, and a portion of the evanescently produced fluorescence is coupled back into the fiber and propagated back to a detector.

A further technique utilizing optical fiber technology involves the optical fiber capillary tube, in which a bare fiber optic is enclosed within a cylindrical fill chamber, producing a sensor element that interacts evanescently with the portion of the fill volume immediately surrounding the fiber. Receptor molecules may be bound to the exposed fiber surface and sandwich or competitive displacement assays may be performed. A light wave would be coupled into the fiber, and a portion of the evanescently induced fluorescence would be coupled back into the fiber and propagated back to a detector. The signal from the target analyte versus the background sources is discriminated by its angular divergence upon exiting the fiber. Other fiber optic techniques such as fiber optic fluorescence may be adapted to the methods disclosed herein utilizing certain of the same principles enunciated above.

Further photonic techniques such as interferometry include the disposition of a thin-film waveguide having, for example, two paths, on the first of which receptor molecules may be immobilized while the second is shielded to provide a reference channel. Laser light, for example, may be coupled into the waveguide and split down the two paths, so that changes in the refractive index and thickness of the covering letter may be detected by the result of a phase shift in the beam, which will, in turn, correlate with the amount of analyte bound. A variation on this approach is identified in the Hartman interferometer, where a single path multi-mode thin film planar waveguide is prepared. Receptor molecules may be immobilized on this path, and light from a laser may be coupled into the waveguide so that two modes propagate down the path. The optics of multimode geometries are such that the higher order mode has a large evanescent field, providing a signal mechanism, and the lower order mode has practically no evanescent field, providing a reference mechanism. Binding with the target analyte will cause related changes in the refractive index and thickness of the covering layer over the path which will be detected by the evanescent field of the higher order mode, causing a phase shift in that mode. As the lower order or reference mode is blind to such changes, no phase shift will be experienced, and the measured difference between the signal and reference beams will be capable of correlation to determine the amount of analyte bound.

While the foregoing discussion has provided both in general terms and some detail, various techniques available in optical sensor technology are adaptable to the practice of the present disclosure. It is to be understood that the above recitation is by no means exhaustive or limitative, as a variety of extant technologies may be adopted, that will successfully measure differences in binding and, consequently, the presence and amount of the respective markers or analytes of interest herein. Of course, as emphasized above, no matter what technology is employed, the practice of the methods disclosed herein comprises simultaneous detection and measurement of at least three analytes.

Immunochromatographic Methods for Detecting PAMG-1

Embodiments of the methods of detecting PAMG-1 according to the present disclosure are described below.

In one embodiment of the method, PAMG-1 is detected in a sample through the contact of a sample containing PAMG-1 with an immunoassay system according to the methods disclosed herein to form an antibody-PAMG-1 complex. The antibody-PAMG-1 complex is then detected. In one variation of this embodiment, the antibody includes a detectable marker, the step of detecting the antibody-PAMG-1 complex, which includes the detectable marker.

In another embodiment of the method, PAMG-1 is detected in a sample by putting the sample in contact with an antibody which has a highly specific binding affinity for PAMG-1 (like M271, exemplified infra), thus forming the antibody M271-PAMG-1 complex. The complex then comes into contact with an immobilized second antibody (e.g., like M52). The second antibody is immunologically distinct from the first antibody (e.g., binds to a different epitope), so that such antibodies can simultaneously bind to the PAMG-1 molecule. The immobilized antibody binds to the mobile antibody PAMG-1 complex to form the immobilized antibody PAMG-1 antibody complex. PAMG-1 is detected by detecting this heterotrimer complex. As noted above, the antibody with high specificity for PAMG-1 is preferably used for the initial recognition of PAMG-1.

When the above-described method includes the use of one antibody of the selected pair labeled with a detectable marker, a variation of the method includes putting the sample in contact with the first, labeled antibody prior to contact of the sample with the second, immobilized antibody. In this variation, the labeled antibody serves to bind to PAMG-1 in the sample. Yet another embodiment of the method includes the following steps: adding a fluid sample containing PAMG-1 to a mobilizable, labeled antibody region of porous material which permits migration of antibodies and proteins therethrough, the antibody region including a mobilizable antibody which has a high specificity for PAMG-1 resulting in the attachment of the antibody to PAMG-1 to form an antibody PAMG-1 complex; migration of the complex to the test region containing a second antibody immobilized therein, which second antibody has a binding affinity for PAMG-1 resulting in the second antibody binding to the labeled antibody-PAMG-1 complex to form an immobilized complex; and detecting the immobilized complex in the test region.

Yet another embodiment of the method is a standard sandwich assay, in which an unlabeled antibody is immobilized on any surface. Addition of fluid sample containing PAMG 1 results in binding of PAMG-1 by the immobilized antibody to form an antibody PAMG-1 complex. Addition of labeled antibody results in formation of an immobilized complex composed of immobilized antibody PAMG-1-labeled antibody and detection of this complex.

According to the above-described methods, the antibodies may include a detectable marker or label, the step of detecting the antibody-PAMG-1 or PAMG-1-antibody complex including detection of the detectable marker or label. Examples of detectable markers that can be used include stained particles, enzymes, dyes and radioactive isotopes. In a specific embodiment, the detectable marker is a stained particle of gold, e.g., having an average dimension between about 20 nm and 30 nm. In yet another embodiment, the detectable marker is horseradish peroxidase.

Exemplary Devices for Detecting PAMG-1

A variety of devices are envisioned for detecting PAMG-1 protein in a sample. Devices and/or methods according to the present disclosure preferably can detect PAMG-1 in a sample where the concentration of PAMG-1 is between about 1 ng/ml and 50 mg/ml, about 2 ng/ml and 50 µg/ml, about 3 ng/ml and 50 mg/ml, or about 4 ng/ml and 50 mg/ml. Non-limiting examples of devices that can be used in the methods disclosed herein are described in U.S. Pat. No. 7,709,272 by Fuks et al. Devices for use in the present methods also include, e.g., a cassette containing a test strip (e.g., with a pad region where the sample is placed, and test region (where results are read)), and optionally, a built-in timer and/or a site to indicate patient identification. The pad and test regions are discussed in more detail below. In certain embodiments of the present methods, the preferred detection threshold of PAMG-1 is adjusted to be at least about 4 ng/ml. It is to be understood that the methods and devices of the present disclosure also encompass PAMG-1 detection thresholds of about at least 1 ng/ml, about at least 2 ng/ml, and about at least 3 ng/ml.

The devices and methods described herein can be adapted to be used easily in a rapid and convenient manner, thereby making it possible for the devices and methods to be used in outpatient conditions. For example, the method can be incorporated into an easy-to-use device that can be operated by a patient with little or no prior experience with the device. This makes the method and device highly reliable and not very susceptible to operator error. The method can also be designed to enable a simple "yes" or "no" (or "+" or "–") determination of the presence of PAMG-1 in a sample (e.g. vaginal fluid sample).

Figure 2:
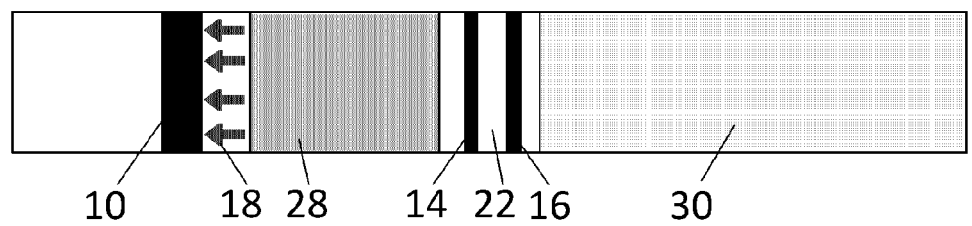

An exemplary, non-limiting device for detecting PAMG-1 is illustrated in FIGS. 1 and 2. For purposes of exemplification, this description refers to monoclonal antibodies exemplified infra. However, it is not necessary that these specific monoclonal antibodies be used. The procedure of selection of, e.g., a pair of PAMG-1 specific antibodies, such as, e.g., those described above, can be reproduced by an artisan of ordinary skill in the art.

As shown in FIGS. 1 and 2, an exemplary device that can be used to perform the methods disclosed herein has a strip-like body composed of several sequentially interconnected elements. More specifically, part 12 of the device comprises a pad, which contains M271 antibody region 10, in which the M271 antibodies are labeled, e.g., by stained particles SP (not shown in the drawings). Pad 12 may be made of a fiberglass tissue or any other material, which is porous and permits the migration of various particles and substances of a sample. Stained particles may comprise gold particles having an average dimension within the range of 20 to 30 nm. The M271 antibody region also contains mouse IgG immunoglobulin labeled by the same stained particles. The labeled M271 antibodies and mouse IgG immunoglobulin are introduced into the band part 10 of pad 12 by impregnating pad 12 with a solution of labeled M271 antibodies and labeled mouse IgG. The solution of M271 antibodies and mouse IgG immunoglobulin may be introduced in nitrocellulose membrane 22 using drawing pen or microdrop forming device. Connected to one end of pad 12 in its longitudinal direction are [a] nitrocellulose membrane 22, which contains a test region 14 and a control region 16. Both the test region 14 and control region 16 are arranged transversely to the device over its entire width. Test region 14 is a band portion of nitrocellulose membrane 22. Test region 14 contains M52 antibodies attached to nitrocellulose membrane 22. Control region 16 contains anti-mouse anti immunoglobulin antibodies attached to nitrocellulose membrane 22. Control region 16 crosses the entire width of strip 22. A filter paper membrane 24 is connected to the end of nitrocellulose membrane 22, which is opposite to the end of nitrocellulose membrane 22 connected to pad 12. A filter paper membrane 24 is connected to the end of nitrocellulose strip 22 in its longitudinal direction. The surface of the device is coated with special protective films 28 and 30, e.g., thin adhesive tapes specially designed for strip devices. Arrows 18 are drawn on the surface of film 28 in order to show the sample application end of pad 12. Pad 12, nitrocellulose membrane 22 and filter paper strip 24 are attached to an adhesive rigid plastic base 26.

In the embodiment described in this section, the device includes an M271 antibody pad region 10 formed of a porous sample application matrix that permits migration of antibodies and proteins therethrough. The M271 antibody region 10 includes the M271 antibody, which is capable of highly specific binding to PAMG-1. Introduction of fluid sample containing PAMG-1 into M271 antibody region results in the attachment of the M271 antibody to PAMG 1 to form the antibody M271-PAMG-1 complex. The device also includes a test region 14 in fluid connection with M271 antibody region 10 formed of a porous material which permits migration of antibodies and proteins therethrough. Test region 14 includes the M52 antibody immobilized in test region 14 which is also capable of binding to PAMG-1. The M52 antibody is immunologically distinct from the M271 antibody such that the M271 and M52 antibodies can simultaneously bind to PAMG-1. Introduction of a fluid sample to the M271 antibody region 10 results in the migration of the antibody M271-PAMG-1 complex into the test region 14 where the antibody M271-PAMG-1 complex binds to the M52 antibody and is immobilized in the test region by the M52 antibody. The device detects PAMG-1 in a sample based on the presence of the M52 antibody immobilized in test region 14. As a result, only PAMG-1 forms an antibody M271-PAMG-1-M52 antibody complex which is immobilized in the test region 14. Thus, the presence of the M52 antibody immobilized in the test region 14 is indicative of the presence of PAMG-1 in the sample.

In this embodiment of a device for detecting PAMG-1 in vaginal secretions, the M271 antibody is attached to a detectable marker which is used to detect PAMG-1 immobilized in the test region 14. Examples of detectable markers that may be used include, but are not limited to, stained particles, enzymes, dyes, fluorescent dyes, and radioactive isotopes. In one embodiment, the detectable marker is gold particles having an average dimension between about 20-30 nm. In one embodiment, the M271 antibody is a labeled antibody in a freeze-dried state.

In a variation of the embodiment where the M271 antibody in the M271 antibody pad region is labeled with a detectable marker, the device further includes test region, which contains the M52 antibody. The pad region and test region are in fluid connection.

In yet another embodiment of the device, also embodied within the device illustrated in FIGS. 1 and 2, the device has a strip-like body with proximal and distal ends. The M271 antibody region 10 of the strip-like body is made of a material which permits the migration of antibodies and proteins therethrough. The M271 antibody region 10 of the strip-like body includes the M271 antibody, which has a highly specific binding affinity for PAMG-1, introduction to the M271 antibody pad region of a fluid sample containing PAMG-1, which results in the attachment of the M271 antibody to PAMG-1 to form the antibody M271-PAMG-1 complex.

The strip-like body also includes a test region 14, which is proximal to the M271 antibody region 10 and is in fluid connection with the M271 antibody region 10. The test region 14 is formed of a material which permits migration of antibodies and proteins therethrough. The test region 14 includes the M52 antibody immobilized in the test region 14, which has a binding affinity for PAMG-1, the introduction of the fluid sample to the M271 antibody region 10 resulting in the migration of the antibody M271-PAMG-1 complex to the test region 14 where the antibody M271-PAMG-1 complex binds to the M52 antibody and is immobilized in test region 14 by the M52 antibody. The test region can also include M42 antibody and M52 antibody immobilized in the test region 14. The device detects PAMG-1 in a sample based on the immobilization of the complex of labeled antibody M271-PAMG-1 in the test region 14. Using various combinations of PAMG-1 specific antibodies (e.g., M42 and M52) immobilized in the test region exemplifies one way to adjust the sensitivity threshold (detection threshold) of the strip device (see U.S. Pat. No. 7,709,272 by Fuks et al.). However, the artisan of ordinary skill in the art will appreciate that other methods of adjusting the detection threshold are possible (e.g., varying the binding affinity of the immobilized and immobilizable antibodies of a pair of PAMG-1 specific antibodies and/or adjusting the procedure, e.g., the procedural timing of the steps of the testing procedure, as disclosed herein).

Control Region. The device can include a standard control region 16 (FIGS. 1 and 2). This control region serves to confirm the proper operation of the device. However, any alternative control-region designs may also be used with a device for use in the methods disclosed herein.

For example, a device with one control region can include the M271 antibody region 10 formed of a material which permits migration of antibodies and proteins therethrough, the M271 antibody region 10 including a labeled M271 antibody that is not immobilized therein and has a high specificity for PAMG-1, introduction to the M271 antibody pad region 10 of a fluid sample containing PAMG-1 resulting in the M271 antibody binding to PAMG-1 to form a antibody M271-PAMG-1 complex. The device can also include a test region 14 in fluid connection with M271 antibody region 10 which is formed of a material which permits migration of antibodies and proteins therethrough. The test region 14 also includes the M52 antibody immobilized in the test region 14 which has a binding affinity for PAMG-1. The M52 antibody is immunologically distinct from the M271 antibody such that the M271 and M52 antibodies can simultaneously bind to PAMG-1. Introduction of the fluid sample to the M271 antibody region 10 results in the migration of the antibody M271-PAMG-1 complex into the test region 14 where the antibody M271-PAMG-1 complex binds to the M52 antibody and is immobilized in test region 14 by the M52 antibody. The device detects PAMG-1 in a sample based on the immobilization of the labeled M271 antibody in the test region 14. When a low concentration of PAMG-1 is present in the sample, at least some of the labeled M271 antibodies migrate from the M271 antibody region 10 through the test region 14 to the control region 16. Anti-mouse anti-immunoglobulin antibodies are immobilized in the control region 16. Anti-immunoglobulin antibodies bind labeled M271 antibodies that stain the control region. If a high concentration of PAMG-1 is present in the sample, then only a low quantity of labeled M271 antibodies can approach the control region 16 and coloration of the control region may be too weak to become visible to the naked human eye. To prevent such a possibility, labeled mouse IgG immunoglobulin was added into M271 antibody region 10. This immunoglobulin does not bind PAMG-1 and migrates freely through M52 antibody test region 14 to the control region 16 where it is bound by anti-mouse antiglobulin antibodies and stains control region 16. The control region confirms the proper functioning of the device regardless of the concentration of PAMG-1 in the sample.

Yet another component of the device can be a porous material that is in tight porous connection with material of test region. This part of device works as a pump that helps to move liquids, proteins and antibodies therethrough. Examples of detectable markers, which may be used for the labeling of mouse antibodies and IgG immunoglobulin include, but are not limited to stained particles, enzymes, dyes, and radioactive isotopes. In one embodiment, the detectable marker is a fluorescent dye. In yet another embodiment, the detectable markers are stained particles. In one embodiment, the M271 antibody, which is a labeled antibody and the labeled mouse immunoglobulin IgG are in a freeze-dried state.

The materials used in the various regions of the above-described device may be any combination of materials that permit the migration of antibodies and proteins therethrough. Examples of suitable materials include but are not limited to fiberglass, porous plastic, nitrocellulose, and filter paper.

The parts of a device for use in a method disclosed herein can be positioned in any functional combination (e.g., in a lateral flow device, cassette, etc.) provided that PAMG-1 can be detected in the sample when present at a concentration of at least a predefined detection threshold (e.g., 4 ng/ml).

Devices for use in the present methods may optionally include a protective film covering at least a portion of the device. It can be transparent or not transparent and can have necessary trademark, informational marks/signs or arrows on its surface.

Sample Collection

In the methods disclosed herein, it is necessary to collect a vaginal fluid sample from a patient. The device or tool or other means used to collect the sample, and transfer the sample to solution (for testing), can be varied according to the present disclosure, so long as the sample is collected. Non-limiting examples of devices for collecting vaginal fluid sample (e.g., a vaginal fluid sample containing PAMG-1), include, e.g., vaginal swabs (e.g., flocked vaginal swabs).

Non-limiting examples of other means to collect a vaginal fluid sample include, e.g., douche method or vaginal wash. Also, a syringe may be used to collect the vaginal fluid sample.

The specific device and/or method of sample collection can be varied, and any suitable device or method known in the art can be used, so long as the vaginal fluid sample is successfully collected. Preferably, the device or means of sample collection yields at least 70%, at least 75%, at least 80%, at least 85%, at least 90%, at least 95%, or greater of the target analyte in the sample (e.g. PAMG-1). For example, the flocked vaginal swab used in the present Examples yields about 80-90% of the PAMG-1 after collection and transfer to solution.

In certain embodiments, the device or means used to collect the vaginal fluid sample provides a 1:1, 1:2, 1:3, 1:4, 1:5, 1:6, 1:7, 1:8, 1:9, or 1:10 dilution of the vaginal fluid sample. In certain embodiments, the device of or means used to collect the vaginal fluid sample provides a dilution of the vaginal fluid sample in the range of 1:1 to 1:10, 1:2 to 1:9, 1:2 to 1:8, 1:2 to 1:7, 1:2 to 1:6, 1:2 to 1:5, 1:2 to 1:4, 1:2 to 1:3, 1:3 to 1:10, 1:3 to 1:9, 1:3 to 1:8, 1:3 to 1:7, 1:3 to 1:6, 1:4 to 1:7, or 1:5 to 1:6.

In a specific embodiment, a vaginal swab provides about a 1:4 dilution of the vaginal fluid sample. In another embodiment, a flocked vaginal swab provides about a 1:4 dilution of the vaginal fluid sample.

Kits

The present disclosure also provides kits. In one aspect a kit disclosed herein comprises a device, e.g., as disclosed herein (e.g., a lateral flow device) for detecting the presence of PAMG-1 in a vaginal fluid sample when present at a level above a predetermined detection threshold (e.g., 0.5 ng/ml, 1 ng/ml, 2 ng/ml, 3 ng/ml, or 4 ng/ml). In another aspect a kit disclosed herein comprises a device (such as, but not limited to a lateral flow device, e.g., such as a device similar to one described in U.S. Pat. No. 7,709,272) for detecting the presence of PAMG-1 in a vaginal fluid sample, when present at a level above a predetermined threshold (e.g., 0.5 ng/ml, 1 ng/ml, 2 ng/ml, 3 ng/ml, or 4 ng/ml); and a means for collecting a vaginal fluid sample (e.g., a vaginal swab, such as, but not limited to, a vaginal swab described herein (e.g., a flocked vaginal swab), a syringe, a douche kit, or other suitable device for collecting the sample). In certain aspects, the means for collecting the vaginal fluid sample can optionally be used to dilute the vaginal fluid sample (e.g., 1:1, 1:2, 1:3, 1:4, 1:5, 1:6, 1:7, 1:8, 1:9, 1:10, or, e.g., in a range of 1:1 to 1:10, 1:2 to 1:9, 1:2 to 1:8, 1:2 to 1:7, 1:2 to 1:6, 1:2 to 1:5, 1:2 to 1:4, 1:2 to 1:3, 1:3 to 1:10, 1:3 to 1:9, 1:3 to 1:8, 1:3 to 1:7, 1:3 to 1:6, 1:4 to 1:7, or 1:5 to 1:6, etc.). The kits can also comprise a solvent for transferring the vaginal fluid sample (e.g., containing an analyte, e.g., PAMG-1), e.g., a solution containing: 0.9% NaCl, 0.01% Triton X100, 0.05% NaN$_3$). The solvent can be contained within a vial that can also be used as applicator of the solvent plus vaginal fluid sample can be applied directly onto a lateral flow device. A kit can also comprise a cassette containing a test strip (e.g., with a pad region where the sample is placed, and test region (where results are read)), and optionally, a built-in timer and/or a site to indicate patient identification. The kits disclosed herein can further comprise one or more vials (e.g., plastic vial) and/or instructions for use. For example, instructions for use can include directions for diagnosing TTD based on the results of the test. The kits can also comprise a desiccant. A kit can also comprise a timer, e.g., built in to the test device, or as a separate unit. The instructions for use can in addition, or alternatively, contain instructions for diagnosing risk of spontaneous rupture of fetal membranes (ROM) (e.g., preterm premature ROM) and/or risk of preterm delivery. The kits can comprises a device as illustrated in FIGS. 1 and 2.

Sample Collection and Test Procedure

In general, the methods and kits disclosed herein can be used to collect specimens (vaginal fluid samples) from patients presenting with signs, symptoms or complaints suggestive of preterm labor. Preferably, the specimen is collected prior to digital examination or lubricants, and prior to use of any disinfectant solutions or medicines or 6 hours after their removal. The specimen can be collected in the presence of non-significant blood admixtures. The methods disclosed herein can be performed even with trace amounts of blood on the collection device (e.g., swab). The specimen can also be collected if urine, semen or vaginal infections are present, and can be collected from patients from 20 to 36 weeks, 6 days, gestational age. Further, speculum examination is not required.

The following methods for collecting a vaginal fluid sample from a pregnant woman and assaying the sample for the presence of PAMG-1 (e.g., for the prediction of TTD and/or for determining a patient's risk of preterm labor and/or spontaneous ROM) according to the present disclosure can be used. Although the skilled artisan will appreciate that different methods and/or test devices can be used to achieve the same results, as disclosed herein, and are also encompassed by the present disclosure.

Sample Collection

In one example of a test according to the present methods, a sample of cervico-vaginal discharge collected by vaginal swab is extracted into a solvent as follows:

Take the solvent (e.g., containing: 0.9% NaCl, 0.01% Triton X100, 0.05% NaN$_3$) vial by its cap and shake well to make sure all liquid in the vial has dropped on the bottom. Open the solvent vial and put it in a vertical position. To collect a sample from the surface of the vagina, a vaginal swab can be used (e.g., a sterile flocked swab), or other suitable collection device or means to collect the vaginal fluid sample, as disclosed above. For vaginal swab, the swab tip should not touch anything prior to its insertion into vagina. Hold the swab in the middle of the stick and, while the patient is lying on her back, carefully insert the swab tip of the swab into the vagina until the fingers contact the skin no more than about 2-3 inches (5-7 cm) deep. Withdraw the swab from the vagina after about 30 seconds (other lengths of time, e.g., about 10, 20, 40, 50, 60, 90, 120 seconds, 3 minutes, 4 minutes, 5 minutes, etc.). Place the swab tip into the vial and rinse the swab in the solvent (e.g., 0.55 ml solvent) by rotating for about 30 seconds (other lengths of time, e.g., about 10, 20, 40, 50, 60, 90, 120 seconds, 3 minutes, 4 minutes, 5 minutes, etc.). Remove and dispose of the swab. The skilled artisan will appreciate that the above procedure and sample collection and transfer of sample to solvent times may vary if other device(s) and/or means or methods are used to collect the vaginal fluid sample. Other such devices and procedures and procedural timing are also encompassed by the present methods.

Test Procedure (PAMG-1 Detection)

Following transferring the vaginal fluid sample obtained from the patient to solution (e.g., by rinsing of the swab in the solvent), contact a PAMG-1 test device, e.g., as disclosed herein, e.g., a lateral flow device, with the solvent. In one embodiment, the sample flows from an absorbent pad to a nitrocellulose membrane, passing through a reactive area containing monoclonal anti-PAMG-1 antibodies conjugated to a gold particle. The antigen-antibody complex flows to the test region where it is immobilized by a second anti-PAMG-1 antibody. This event leads to the appearance of a test line. Unbound antigen-antibody complexes continue to flow along the test strip and are immobilized by a second antibody. This leads to the appearance of an internal control line. In one embodiment, the test strip is dipped into the vial with solvent for about 5 minutes (other lengths of time, e.g., about 1, 2, 3, 4, 6, 7, 8, 9, 10 minutes, are also contemplated herein, depending upon the specific conditions of the test and the specific method or device used to test the sample). The test strip can be removed as soon as two stripes are clearly visible in the vial (about 5 minutes). The results can then be read (e.g., by placing the test on a clean, dry, flat surface). In one embodiment, the presence of two lines indicates a positive test result (PAMG-1 detected) and the presence of one line indicates a negative result. The skilled artisan will appreciate that the above procedural steps and timing are exemplary only, and are not limiting.

As discussed above, it is to be understood that variations of this procedure are also encompassed by the present disclosure, so long as they result in the detection of PAMG-1 in the vaginal fluid sample when present at a predefined detection threshold (e.g., about at least 4 ng/ml, about at least 3 ng/ml, about at least 2 ng/ml, or about at least 1 ng/ml). Thus, for example, the type and volume of solvent, device or means for sample collection, and PAMG-1 detection device can be varied or completely different from those disclosed as examples herein. The incubation times above, e.g., 30 second sample collection with swab, 30 second rinse of swab in solvent may vary depending on the specific procedure and test device used. The site of vaginal fluid sample collection can vary, and can be determined by one of ordinary skill in the art. By way of non-limiting example, exemplary sites of collection of vaginal fluid samples include collection from, e.g., cervical os, cervical canal, posterior fornix, vaginal cavity/canal. Collection of the sample can be blind (i.e., collected from the vagina without use of a speculum).

In accordance with the present disclosure, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

The following examples are meant to illustrate, not limit, the present disclosure.

EXAMPLES

Example 1

PAMG-1 Detection Kit (TTD Test)

A kit for the detection of PAMG-1 at a detection threshold of 4 ng/ml was prepared. The kit included a diagnostic device employing monoclonal antibodies that detect PAMG-1 present in cervico-vaginal secretions, as described in detail in U.S. Pat. No. 7,709,272 by Fuks et al. The diagnostic device is illustrated in FIGS. 1 and 2. The diagnostic device itself can detect PAMG-1 when present at a concentration of at least 1 ng/ml in the sample. The kit also included a flocked vaginal swab with the following specifications: length of the plastic shaft: 170.0 mm±1 mm; plastic tip diameter: 4.6 mm±0.1 mm; stick diameter handle part: 4.4 mm±0.2 mm; length of the fibre tip: 22 mm±3 mm; flocked tip diameter: 7.00 mm±1.5 mm; total length: 171 mm±2 mm. The kit further included instructions for sample collection and the testing procedure. The sample collection and testing procedure included a 30 second swab saturation in the vagina (a sterile speculum examination was not required), a 30 second active washing step whereby the swab just removed from the vagina was actively rotated in a solvent filled vial and a 5 minute waiting period from the time the swab was removed and the test strip was inserted if two testing lines did not appear sooner. During the test procedure, PAMG-1 present in the sample sequentially bound to monoclonal antibody conjugated with labeled particles, then to monoclonal antibody immobilized on an insoluble carrier. The in vivo sensitivity detection threshold of PAMG-1 was adjusted to 4 ng/ml using the specific sample collection and TTD test procedure described below:

Sample Collection and TTD Test Procedure:
1. Take the solvent (containing: 0.9% NaCl, 0.01% Triton X100, 0.05% $NaN_3$) vial by its cap and shake well to make sure all liquid in the vial has dropped on the bottom. Open the solvent vial and put it in a vertical position.
2. To collect a sample from the vagina use the sterile flocked swab provided with the TTD kit. Remove the sterile flocked swab from its package following instructions on the package. The swab tip should not touch anything prior to its insertion into vagina. Hold the swab in the middle of the stick and, while the patient is lying on her back, carefully insert the swab tip of the swab into the vagina until the fingers contact the skin no more than 2-3 inches (5-7 cm) deep. Withdraw the swab from the vagina after 30 seconds.
3. Place the swab tip into the vial and rinse the swab in the solvent by rotating for 30 seconds. Remove and dispose of the swab.
4. Tear open the foil pouch at the tear notches and remove the PAMG-1 test strip.
5. Dip the white end of the test strip (marked with arrows) into the vial with solvent for no more than 5 minutes.
6. Remove the test strip if two stripes are clearly visible in the vial (no later than 5 minutes sharp). Read the results by placing the test on a clean, dry, flat surface.
7. Do not read or interpret the results after 10 minutes have passed since dipping the test strip into the vial.
8. The presence of two lines indicates a positive test result (positive for PAMG-1) and the presence of one line indicates a negative test result (negative for PAMG-1).

Example 2

Clinical Trial for Predicting Time to Delivery (TTD)

A prospective observational clinical trial using the PAMG-1 detection kit described in Example 1, above (referred to below as a TTD Test Kit), was run in order to assess the efficacy of the TTD test kit for predicting TTD, based on the detection of PAMG-1 in the cervico-vaginal secretions of pregnant women between $20^{0/7}$ and $36^{6/7}$ weeks gestational age presenting with signs and symptoms of PTL and having clinically intact membranes.

Study Design:

The following study design is used:
1. Assessments are stratified by the following gestational age ranges:
   a. <22 weeks
   b. $22-34^{6/7}$ weeks
   c. $35-36^{6/7}$ weeks The TTD kit for the detection of PAMG-1 is compared to other methods available in assessing time to delivery in the same patient population, including:
   a. cervical length measurements by trans-vaginal ultrasound (<30 mm)
   b. cervical dilatation >1 cm
   c. contraction Frequency ≥8 per hour
2. Data Analysis The association between the results of the TTD test, cervical length, and the following outcomes are determined:
   a. Delivery <37 weeks gestation
   b. Admission to neonatal intensive care unit (NICU)
   c. Histological chorioamnionitis
   d. Funisitis
   e. Respiratory distress syndrome
   f. Patent ductus arteriosus
   g. Neonatal sepsis
   h. Birth weight
   i. Perinatal death
3. Selection and Withdrawal of Subjects:

The following includes and exclusion criteria was used:
Inclusion Criteria: Women between $20^{0/7}$ and $36^{6/7}$ weeks of gestation with ≤3 cm cervical dilatation, presenting with self-reported signs, symptoms or complaints suggestive of preterm labor (outlined below) are invited to participate in the trial:
   a. Uterine contractions, with or without pain
   b. Intermittent lower abdominal pain
   c. Dull backache
   d. Pelvic pressure
   e. Bleeding during the second or third trimester
   f. Menstrual-like or intestinal cramping, with or without diarrhea
   g. Absence of leakage from the cervical os observed via a sterile speculum examination Exclusion Criteria: During the clinical examination at enrollment, subjects who are found to have one of the following are deemed ineligible and are not included in the analysis:
   a. Presented for regularly scheduled obstetrical care with complaints of symptoms (i.e., the symptoms were not strong enough in the patient's opinion to warrant unscheduled emergency evaluation of her condition, such as would be provided in a hospital Labor and Delivery Unit or Emergency Room)
   b. Received tocolytic medications for treatment of threatened preterm delivery prior to collection of the cervicovaginal specimens or cervical length measurements
   c. Cervical dilatation >3 centimeters
   d. Suspected placenta previa
   e. $<20^{0/7}$ weeks of gestation or ≥37 weeks of gestation
   f. Overt rupture of the fetal membranes (ROM) as indicated by visualized leakage of fluid from the cervical os
   g. Cervical cerclage in place
   h. A symptom not associated with idiopathic threatened preterm delivery (e.g. trauma)
   i. Digital exam prior to specimen collection
   j. Enrollment in a tocolytic study
   k. Heavy vaginal bleeding
   l. <18 yrs old and not emancipated consenting minor All patients undergoing labor augmentation to enhance the progression of labor or who have a cesarean section delivery before active labor is diagnosed (defined as regular contractions every 10 minutes or less, lasting more than 40 seconds, with cervical effacement more than 80 percent and dilation of 2 cm (or 3 cm)) are not included in the analysis.

4. Endpoints

Sensitivity (SN), specificity (SP), positive predictive value (PPV), and negative predictive value (NPV) for the TTD test, cervical length measurements by trans-vaginal ultrasound (<30 mm), cervical dilatation >1 cm, and contraction frequency ≥8 per hour for the following presentation-to-delivery time intervals are determined:
   a. ≤48 hours
   b. ≤7 days
   c. ≤14 days 5. Study Procedure The following study procedure is followed:
   a. Patients presenting with signs and symptoms of PTL who report no intercourse within past 24 hours and were between $20^{0/7}$ and $36^{6/7}$ weeks of gestation sign informed consent.
   b. Specimen for the TTD test is collected (as described in Example 1, above) prior to the insertion of a sterile speculum examination in accordance with manufacturer's recommendations.
   c. The sample is appropriately labeled and stored in a specially designated place in accordance with manufacturer recommendations for later examination by a separate investigator who was blinded to the results of the physician's regular clinical evaluation.
   d. After collecting the above-indicated sample, the physician completes the physical examination of the patient to determine whether the patient would be included or excluded from the clinical trial based on the inclusion and exclusion criteria set forth above.
   e. Physician records the findings.
   f. Cervical length measurement by transvaginal ultrasound (TVU) is performed and results are recorded.
   g. Patient delivery data (e.g. time, condition, etc.) are recorded.
   h. The collected sample is tested using the TTD test described in Example 1.

6. Statistical Analysis

Mann-Whitney U test, Kaplan-Meier survival analysis and Cox regression are used for evaluation of the primary outcome. PPV, NPV, SN, and SP are calculated for the TTD test (for all time points tested). 95% confidence intervals (CI) are computed using the Clopper-Pearson procedure.

7. Site Diagnosis and Management of Confirmed Preterm Labor Patient

In accordance with the ACOG Practice Bulletin on the Management of Preterm Labor (2003), the patient diagnosed with PTL may be treated with one or more of the below:
   a. Tocolytic therapy
   b. Antibiotics
   c. Bed Rest
   d. Corticosteroids Of the above possible combinations of diagnostic and treatment options listed above, there is no supporting evidence indicating that any have an effect on the primary outcome measure of this study (which is the presentation-to-delivery time interval).

Results:

The expected results (based on present data) of an ongoing clinical trial are summarized in Table 3, below:

TABLE 2

Expected Results of Clinical Trial

| TTD (days) | NPV (%) (95% CI*) | PPV (%) (95% CI*) | SN (%) (95% CI*) | SP (%) (95% CI*) |
|---|---|---|---|---|
| ≤2 | 100.0 (0.954, 1.00) | 45.5 (0.244, 0.678) | 100.0 (0.692, 1.00) | 86.7 (0.779, 0.929) |
| ≤7 | 97.4 (0.910, 0.997) | 81.8 (0.597, 0.948) | 90.0 (0.683, 0.988) | 95.0 (0.877, 0.986) |
| ≤14 | 93.6 (0.857, 0.979) | 90.9 (0.708, 0.988) | 80.0 (0.593, 0.932) | 97.3 (0.907, 0.997) |

Table Legend:
"TTD": time-to-delivery";
"SN": sensitivity;
"SP": specificity;
"NPV": negative predictive value;
"PPV": positive predictive value;
*95% confidence intervals (CI) computed via the Clopper-Pearson procedure.

Final Results of Completed Clinical Trial

In the clinical trial, 101 women with singleton pregnancies between $20^{0/7}$ and $36^{6/7}$ week of gestation presenting with self-reported signs, symptoms or complaints suggestive of preterm labor including uterine contractions, with or without pain, intermittent lower abdominal pain and pelvic pressure were evaluated over the course of the study. The recruited patients had clinically intact amniotic membranes as determined by speculum examination and minimal cervical dilatation (≤3 cm). A full clinical examination was conducted by the attending physician, including collection of the TTD test sample as described in Example 1, above. Parameters recorded at presentation included cervical length, cervical dilatation, contraction frequency, membrane status, cervical effacement, patient history, and TTD Test Kit test result. Patients with overt rupture of fetal membranes, diagnosed as fluid seen leaking from the cervical os during the sterile speculum examination, were not enrolled in the study. The median age was 28 years (range: 18-43 years), and the median gestational age at presentation was 31.4 weeks (range: 22.4-36.5 weeks). No multiple gestations were included in the trial.

The TTD test sample was collected and the TTD test procedure was performed as described in Example 1, above. The result was interpreted once two lines were visible, or after five minutes elapsed since the insertion of the test strip into the sample vial. The results were reported by the presence of two lines (positive for PAMG-1) or one line (negative for PAMG-1). The attending physician was not aware of the TTD test results when making decisions about the care of the patient. Sensitivity (SN), specificity (SP), positive predictive value (PPV), and negative predictive value (NPV) of the TTD test kit in predicting time to spontaneous preterm delivery (within 7 and 14 days) were calculated at the conclusion of the trial. 95% confidence intervals were calculated using the Clopper-Pearson procedure.

Twenty (20) patients delivered within 7 days of presentation and an additional five delivered within 14 days of presentation. The TTD Test was positive in 23% (23/101) of patients and the median test-to-delivery interval in this population was 3.86 days compared to 32.12 days for the TTD test negative group. Table 3, below, summarizes the TTD test results for delivery within 7 and 14 days, respectively.

TABLE 3

Results of TTD Test

| | | Delivery ≤7 days (no. patients) | | Delivery ≤14 days (no. patients) | |
|---|---|---|---|---|---|
| | | + | − | + | − |
| TTD Test Results | + | 18 | 5 | 20 | 3 |
| | − | 2 | 76 | 5 | 73 |

The NPV, PPV, SN and SP for the TTD Test confirming spontaneous preterm delivery within 7 and 14 days of presentation are summarized in Table 4, below:

TABLE 4

NPV, PPV, SN and SP of TTD Test

| TTD (days) | NPV (95% CI*) | PPV (95% CI*) | SN (95% CI*) | SP (95% CI*) |
|---|---|---|---|---|
| ≤7 | 97.4% (91.0-99.7%) | 78.3% (56.3-92.5%) | 90.0% (68.3-98.8%) | 93.8% (86.2-98.0%) |
| ≤14 | 93.6% (85.7-97.9%) | 87.0% (66.4-97.2%) | 80.0% (59.3-93.2%) | 96.1% (88.9-99.2%) |

Table Legend:
"TTD": time-to-delivery;
"SN": sensitivity;
"SP": specificity;
"NPV": negative predictive value;
"PPV": positive predictive value
*95% confidence intervals (CI) computed via the Clopper-Pearson procedure.

The final NPV, PPV, SN and SP results for the TTD test for delivery within 48 hours (≤2 days) were the same as the expected results set forth in Table 2, above.

The incidence of a positive TTD test was also broken down by different gestational age week ranges. The results are summarized in Table 5, below:

TABLE 5

Positive TTD Test Incidence and Performance by Gestational Age

| Gestational Age Week Interval (inclusive) | TTD Test | | Delivery ≤7 days | | | |
|---|---|---|---|---|---|---|
| | Total | Positive Incidence | SN | SP | PPV | NPV |
| 22-25 | 6 | 0.0% | N/A | 100.0% | N/A | 100.0% |
| 26-29 | 31 | 25.8% | 100% | 92.0% | 75.0% | 100.0% |
| 30-33 | 37 | 24.3% | 100% | 90.3% | 66.7% | 100.0% |
| 34-36 | 27 | 22.2% | 75% | 100.0% | 100.0% | 90.5% |

Table Legend:
"TTD": time-to-delivery;
"SN": sensitivity;
"SP": specificity;
"NPV": negative predictive value;
"PPV": positive predictive value This Example, including the data shown in Tables 2-5, demonstrated that the TTD test provides a method for diagnosing TTD within 2, 7 or 14 days, with high SN, SP, NPV, and PPV. It was demonstrated that the TTD test can be used to rule out spontaneous preterm delivery within 2, 7 and 14 days in patients with threatened preterm labor. A positive TTD test in patients presenting with symptoms of preterm labor, intact membranes, and minimal cervical dilatation (≤3 cm) indicated spontaneous preterm delivery would occur within 7 days with a high degree of accuracy. A negative result, furthermore, indicated that spontaneous preterm delivery within 14 days was highly unlikely. The Examples also demonstrates that the TTD test has a high PPV, NPV, SN and SP.

A number of embodiments of the present disclosure have been described. Nevertheless, it will be understood that various modifications may be made without departing from the spirit and scope of the methods disclosed herein. It is further to be understood that all values are approximate, and are provided for description. Accordingly, other embodiments are within the scope of the following claims.

What is claimed is:

1. A method for determining the risk of preterm delivery, the method comprising:
   (a) selecting a pregnant woman for analysis by the method only if the pregnant woman presents with one or more of the following:
      (i) signs, symptoms or complaints suggestive of preterm labor;
      (ii) a gestational age between 20 weeks and 36 weeks, 6 days;
      (iii) a cervical length of 25 mm or more; and
      (iv) a cervical dilatation of 3 cm or less;
   (b) collecting a vaginal fluid sample from the pregnant woman with a flocked swab;
   (c) providing a dilution of the fluid sample from the flocked swab of between 1:1 and 1:10;
   (d) contacting the diluted vaginal fluid sample obtained from the pregnant woman with at least two PAMG-1-specific monoclonal antibodies, wherein one or more of the at least two PAMG-1-specific monoclonal antibodies is an antibody selected from the group consisting of M271, produced by hybridoma N271, deposited with the Russian National Collection of Industrial Microorganisms (VKPM) Depository and assigned accession number VKPM-93; and M52, produced by hybridoma N52, deposited with the VKPM and assigned accession number VKPM-92; and M42, produced by hybridoma N42, deposited with the VKPM and assigned accession number VKPM-94; and wherein at least one of the antibodies binds to PAMG-1 when present in the sample to form a PAMG-1 / monoclonal antibody complex;
   (e) detecting the presence of the PAMG-1/ monoclonal antibody complex in the sample only when the concentration of PAMG-1 in the sample is at least 4 ng/ml; and
   (f) diagnosing that the pregnant woman is at risk of preterm delivery if PAMG-1 is detected; or
   (g) diagnosing that the pregnant woman is not at risk of preterm delivery if PAMG-1 is not detected.

2. The method of claim 1, comprising contacting the flocked swab with a solvent to release the collected vaginal fluid sample.

3. The method of claim 1, comprising collecting the vaginal fluid sample over a time period of about 30 seconds.

4. The method of claim 2, comprising contacting the flocked swab with the solvent for about 30 seconds after collecting the vaginal fluid sample.

5. The method of claim 1, wherein the vaginal fluid sample is contacted with the at least two PAMG-1-specific monoclonal antibodies for 5 minutes.

6. The method of claim 1, wherein the at least two PAMG-1 specific monoclonal antibodies are used in a lateral flow device.

7. The method of claim 6, wherein the lateral flow device comprises a pad region and a test region.

8. The method of claim 7, wherein the pad region of the test device comprises one of the at least two PAMG-1 specific monoclonal antibodies and the test region comprises the other of the two, and wherein the PAMG-1 specific monoclonal antibody in the pad region is mobilizable and the PAMG-1 specific monoclonal antibody in the test region is immobilized.

9. The method of claim 8, wherein the test region of the test device further comprises a control region.

10. The method of claim 1, wherein the [flocked swab provides a] dilution of [any PAMG-1 present in] the vaginal fluid sample is 1:4 [in a range of 1:1 to 1:10].

11. The method of claim 1, wherein the risk if PAMG-1 is detected, is of preterm delivery within 7 days.

12. The method of claim 1, wherein the risk if PAMG-1 is detected, is of preterm delivery within 14 days.

* * * * *